US012077813B2

(12) United States Patent
Patel et al.

(10) Patent No.: US 12,077,813 B2
(45) Date of Patent: *Sep. 3, 2024

(54) METHODS AND SYSTEMS FOR SAMPLE ANALYSIS

(71) Applicant: N6 TEC, INC., Pleasanton, CA (US)

(72) Inventors: Pranav Patel, Pleasanton, CA (US); Yassine Kabouzi, Pleasanton, CA (US); Amir Sadri, Markham (CA); Yann Jouvenot, Benicia, CA (US)

(73) Assignee: N6 TEC, INC., Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/364,429

(22) Filed: Aug. 2, 2023

(65) Prior Publication Data

US 2023/0374578 A1 Nov. 23, 2023

Related U.S. Application Data

(63) Continuation of application No. PCT/US2022/044540, filed on Sep. 23, 2022.

(60) Provisional application No. 63/247,397, filed on Sep. 23, 2021.

(51) Int. Cl.
  *C12Q 1/68* (2018.01)
  *C12Q 1/686* (2018.01)

(52) U.S. Cl.
  CPC .................. *C12Q 1/686* (2013.01)

(58) Field of Classification Search
  None
  See application file for complete search history.

(56) References Cited

U.S. PATENT DOCUMENTS

| | | | |
|---|---|---|---|
| 6,699,713 B2 | 3/2004 | Benett et al. | |
| 6,938,476 B2* | 9/2005 | Chesk | G01F 23/24 73/304 R |
| 7,081,226 B1 | 7/2006 | Wittwer et al. | |
| 7,164,077 B2 | 1/2007 | Venkatasubramanian | |
| 8,017,380 B2 | 9/2011 | Moriwaki et al. | |
| 8,110,396 B2 | 2/2012 | Bommer et al. | |
| 8,252,881 B2* | 8/2012 | Ma | C08F 283/12 528/25 |
| 8,389,288 B2 | 3/2013 | Heimberg et al. | |
| 8,676,383 B2 | 3/2014 | Tan et al. | |
| 8,815,162 B2 | 8/2014 | Vossenaar et al. | |
| 9,268,346 B2 | 2/2016 | Moriwaki et al. | |
| 9,446,410 B2 | 9/2016 | Evans et al. | |
| 9,457,351 B2 | 10/2016 | Tan et al. | |
| 9,475,051 B2 | 10/2016 | Segawa et al. | |
| 10,583,442 B2 | 3/2020 | Hasson et al. | |
| 10,814,326 B2 | 10/2020 | Ozawa et al. | |
| 10,907,202 B2 | 2/2021 | Smith et al. | |
| 11,142,785 B2 | 10/2021 | Handique et al. | |
| 11,376,599 B2 | 7/2022 | Evans et al. | |
| 2002/0058282 A1 | 5/2002 | McMillan et al. | |
| 2005/0009070 A1 | 1/2005 | Arciniegas et al. | |
| 2005/0064582 A1 | 3/2005 | Wittwer et al. | |
| 2005/0129582 A1 | 6/2005 | Breidford et al. | |
| 2006/0286558 A1 | 12/2006 | Novoradovskaya et al. | |
| 2010/0122807 A1 | 5/2010 | Harttig | |
| 2013/0078610 A1 | 3/2013 | Kimball et al. | |
| 2015/0212032 A1 | 7/2015 | Holt et al. | |
| 2017/0157613 A1 | 6/2017 | Li et al. | |
| 2019/0046988 A1 | 2/2019 | Chattopadhyay et al. | |
| 2021/0291190 A1 | 9/2021 | Newman-Lehman et al. | |
| 2021/0293707 A1 | 9/2021 | Frank et al. | |

(Continued)

FOREIGN PATENT DOCUMENTS

| | | |
|---|---|---|
| EP | 0912760 A2 | 5/1999 |
| GB | 2472455 A | 2/2011 |
| WO | WO-99/48608 A2 | 9/1999 |

(Continued)

OTHER PUBLICATIONS

Mondal, S. and Venkataraman, V., 2005. In situ monitoring of polymerase extension rate and adaptive feedback control of PCR by using fluorescence measurements. Journal of biochemical and biophysical methods, 65(2-3), pp. 97-105. (Year: 2005).*

Mondal, S. and Venkataraman, V., 2007. Novel fluorescence detection technique for non-contact temperature sensing in microchip PCR. Journal of Biochemical and Biophysical methods, 70(5), pp. 773-777. (Year: 2007).*

International search report with written opinion dated Feb. 22, 2023 for PCT/US2022/044540.

Co-pending U.S. Appl. No. 18/364,944, inventors Patel; Pranav et al., filed Aug. 3, 2023.

(Continued)

*Primary Examiner* — Stephanie K Mummert
*Assistant Examiner* — Olayinka A Oyeyemi
(74) *Attorney, Agent, or Firm* — Wilson Sonsini Goodrich & Rosati

(57) ABSTRACT

The present disclosure provides methods and systems comprising use of a device. A device may comprise a plurality of locations configured to contain one or more samples, a plurality of thermal elements corresponding and disposed adjacent to the plurality of locations, wherein the plurality of elements are configured to affect a thermal condition within individual locations of the plurality of locations, at least one additional thermal element operably coupled and common to at least a subset of the plurality of elements, wherein the additional thermal element is configured to affect at least one operating condition of the plurality of thermal elements at least partially in response to the thermal condition within the individual locations of the plurality of locations, and at least one optical system configured to detect a signal or change thereof from the individual locations of the plurality of locations, wherein the signal or change thereof is generated at least partially by a change of the thermal condition and is indicative of a property associated with the one or more samples.

20 Claims, 26 Drawing Sheets

(56) References Cited

U.S. PATENT DOCUMENTS

2021/0308684 A1  10/2021  Davis

FOREIGN PATENT DOCUMENTS

| | | |
|---|---|---|
| WO | WO-2004085065 A1 | 10/2004 |
| WO | WO-2020014400 A1 | 1/2020 |
| WO | WO-2020190035 A1 | 9/2020 |
| WO | WO-2021150984 A1 | 7/2021 |
| WO | WO-2023049349 A1 | 3/2023 |

OTHER PUBLICATIONS

Grace, Marcy, et al., Development and Assessment of a Quantitative Reverse Transcription-PCR Assay for Simultaneous Measurement of Four Amplicons. Clinical Chemistry 49(9): 1467-1475 (2003).

Green, Michael, et al., Analysis and Normalization of Real-Time Polymerase Chain Reaction (PCR) Experimental Data. Cold Spring Harbor Protocols 769-777 (2018).

Grunenwald, Haiying, Optimization Of Polymerase Chain Reactions. PCR Protocols 89-99 (2003).

Hua, Zhishan, et al., Multiplexed Real-Time Polymerase Chain Reaction on a Digital Microfluidic Platform. Analytical Chemistry 82(6):2310-2316 (2010).

Kontanis, Elias, et al., Evaluation of Real-Time PCR Amplification Efficiencies to Detect PCR Inhibitors. Journal of Forensic Sciences 51(4):795-804 (2006).

Neuzil, Pavel, et al., Ultra Fast Miniaturized Real-time PCR: 40 Cycles in Less Than Six Minutes. Nucleic Acids Research 34(11):1-9 (2006).

U.S. Appl. No. 18/364,944 Office Action dated Mar. 14, 2024.

Wang, Chih, et al., Circulating Polymerase Chain Reaction Chips Utilizing Multiple-membrane Activation. Journal of Micromechanics and Microengineering 17(2):367-375 (2007).

* cited by examiner

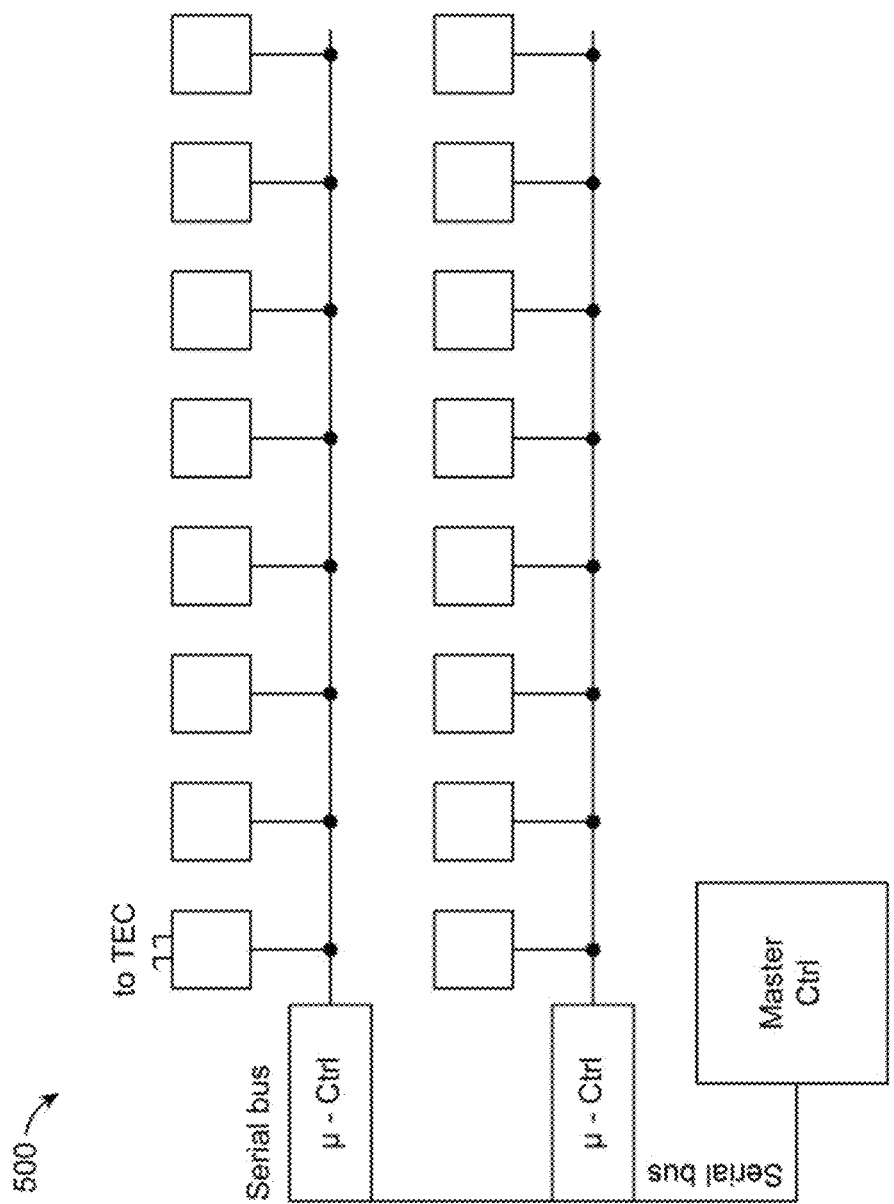

PROTOCOL

Default ▽    Saad Gradient ▽

Volume | 50 | ul

Lid Temp | 105.0 | °C

Step 1 | + | × | 95.0 | °C | 60.0 | Sec

Step 2 | + | × | gradient | 2.00 | Min

Step 3 | + | × | 72.0 | °C | 60.0 | Sec

FIG. 24A

PLATE SETUP

Ramp rate | 2 | °C/sec

| 50.0 | 50.0 | 50.0 | 50.0 | 50.0 | 50.0 | 50.0 | 50.0 | 50.0 | 30.0 | 50.0 | 50.0 |
|---|---|---|---|---|---|---|---|---|---|---|---|
| 50.0 | 50.0 | 50.0 | 50.0 | 50.0 | 50.0 | 50.0 | 50.0 | 50.0 | 30.0 | 50.0 | 50.0 |
| 50.0 | 50.0 | 50.0 | 50.0 | 50.0 | 50.0 | 50.0 | 50.0 | 50.0 | 37.1 | 56.4 | 50.0 |
| 50.0 | 50.0 | 50.0 | 50.0 | 50.0 | 50.0 | 50.0 | 50.0 | 50.0 | 44.3 | 62.9 | 50.0 |
| 50.0 | 50.0 | 50.0 | 50.0 | 50.0 | 50.0 | 50.0 | 50.0 | 50.0 | 51.4 | 69.3 | 50.0 |
| 50.0 | 50.0 | 50.0 | 50.0 | 50.0 | 50.0 | 50.0 | 50.0 | 50.0 | 58.6 | 75.7 | 50.0 |
| 50.0 | 50.0 | 50.0 | 50.0 | 50.0 | 50.0 | 50.0 | 50.0 | 50.0 | 65.7 | 82.1 | 50.0 |
| 50.0 | 50.0 | 50.0 | 50.0 | 50.0 | 50.0 | 50.0 | 50.0 | 50.0 | 72.9 | 88.6 | 50.0 |
| 50.0 | 50.0 | 50.0 | 50.0 | 50.0 | 50.0 | 50.0 | 50.0 | 50.0 | 80.0 | 95.0 | 50.0 |
| 50.0 | 50.0 | 50.0 | 50.0 | 50.0 | 50.0 | 50.0 | 50.0 | 50.0 | 80.0 | 95.0 | 50.0 |

■ GRADIENT SETUP
○ Rows
○ Individual Rows
○ Column
● Individual Column
○ Whole Plate

FIG. 24B

METHODS AND SYSTEMS FOR SAMPLE ANALYSIS

CROSS-REFERENCE

This application is a continuation of International Patent Application No. PCT/US22/44540 filed Sep. 23, 2022, which claims the benefit of U.S. Provisional Application No. 63/247,397 filed Sep. 23, 2021, each of which is incorporated herein by reference in its entirety.

BACKGROUND

Diagnostic testing methods and devices have become an important part of modern medical care. Polymerase chain reaction (PCR) based diagnostics have grown in importance as global attention has been drawn to the health problems created by hard to identify pathogens.

SUMMARY

In an aspect, the present disclosure provides a method for performing a polymerase chain reaction (PCR) analysis of a sample containing or suspected of containing an analyte, comprising: (a) providing the sample to a location of a substrate, wherein the location has a volume configured to retain the sample and permit the sample to be subjected to a condition for the PCR analysis; (b) using a first element disposed adjacent to the location to affect the condition in the location to thereby initiate the PCR reaction using the sample, wherein the PCR reaction generates a signal or signal change which is indicative of a property associated with the analyte; (c) using a second element operably coupled to the first element to adjust an operating condition of the first element at least partially in response to the signal or signal change, to thereby affect the condition in the location; and (d) adjusting the operating condition of the first element to stop the PCR reaction upon the signal or signal change reaching a predetermined threshold.

In some embodiments, a second location of the device comprises a second sample. In some embodiments, a second PCR reaction continues within the second location after the PCR reaction in the first location is stopped. In some embodiments, the method does not comprise pre-normalization. In some embodiments, the method does not comprise pre-quantification. In some embodiments, a presence or the absence of the analyte is determined with a sensitivity of at least about 90%. In some embodiments, a presence or the absence of the analyte is determined with a specificity of at least about 90%. In some embodiments, a presence or the absence of the analyte is determined with an accuracy of at least about 90%. In some embodiments, the signal or signal change comprises an optical signal or a change thereof. In some embodiments, the property is a presence, an absence, an amount, or a concentration of the analyte.

In another aspect, the present disclosure provides a device for sample detection and analysis, comprising: a plurality of locations configured to contain one or more samples; a plurality of thermal elements corresponding and disposed adjacent to the plurality of locations, wherein the plurality of elements are configured to affect a thermal condition within individual locations of the plurality of locations; at least one additional thermal element operably coupled and common to at least a subset of the plurality of elements, wherein the additional thermal element is configured to affect at least one operating condition of the plurality of thermal elements at least partially in response to the thermal condition within the individual locations of the plurality of locations; and at least one optical system configured to detect a signal or change thereof from the individual locations of the plurality of locations, wherein the signal or change thereof is generated at least partially by a change of the thermal condition and is indicative of a property associated with the one or more samples. In some embodiments, each element of the plurality of elements may be associated with a different temperature sensor.

In some embodiments, the device further comprises a substrate which comprises the plurality of locations. In some embodiments, the plurality of locations are a plurality of chambers, or a plurality of microfluidic channels. In some embodiments, the substrate is a multi-well plate, and wherein the plurality of locations are wells comprised in the multi-well plate. In some embodiments, the individual locations of the plurality of locations are spatially distinguishable and independently addressable. In some embodiments, individual thermal elements of the plurality of thermal elements are configured to independently affect thermal conditions within the individual locations of the plurality of locations. In some embodiments, the plurality of thermal elements comprise a plurality of thermoelectric heating or thermoelectric cooling elements. In some embodiments, the at least one additional thermal element comprises at least one thermoelectric heater or at least one thermoelectric cooler. In some embodiments, each location of the plurality of locations is maintained at a temperature of less than about 1 degree Celsius from a set temperature of the location. In some embodiments, the plurality of locations comprises at least about 96 locations. In some embodiments, the plurality of locations comprises at least about 384 locations. In some embodiments, the device is configured to temperature cycle a first subset of the plurality of locations while maintaining a second subset of the plurality of locations at a constant temperature. In some embodiments, the device is configured to generate a condition profile across the plurality of locations. In some embodiments, the profile is a temperature profile. In some embodiments, the device further comprises one or more heat pipes configured to reduce thermal crosstalk between the plurality of locations. In some embodiments, the optical system is configured to detect the signal or change thereof from the each location of the plurality of locations individually.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 5 is a schematic of an addressable control array, according to an embodiment.

FIGS. 24A-24B show software setting for the experiment performed in FIG. 23, according to some embodiments.

DETAILED DESCRIPTION

Figure 1:
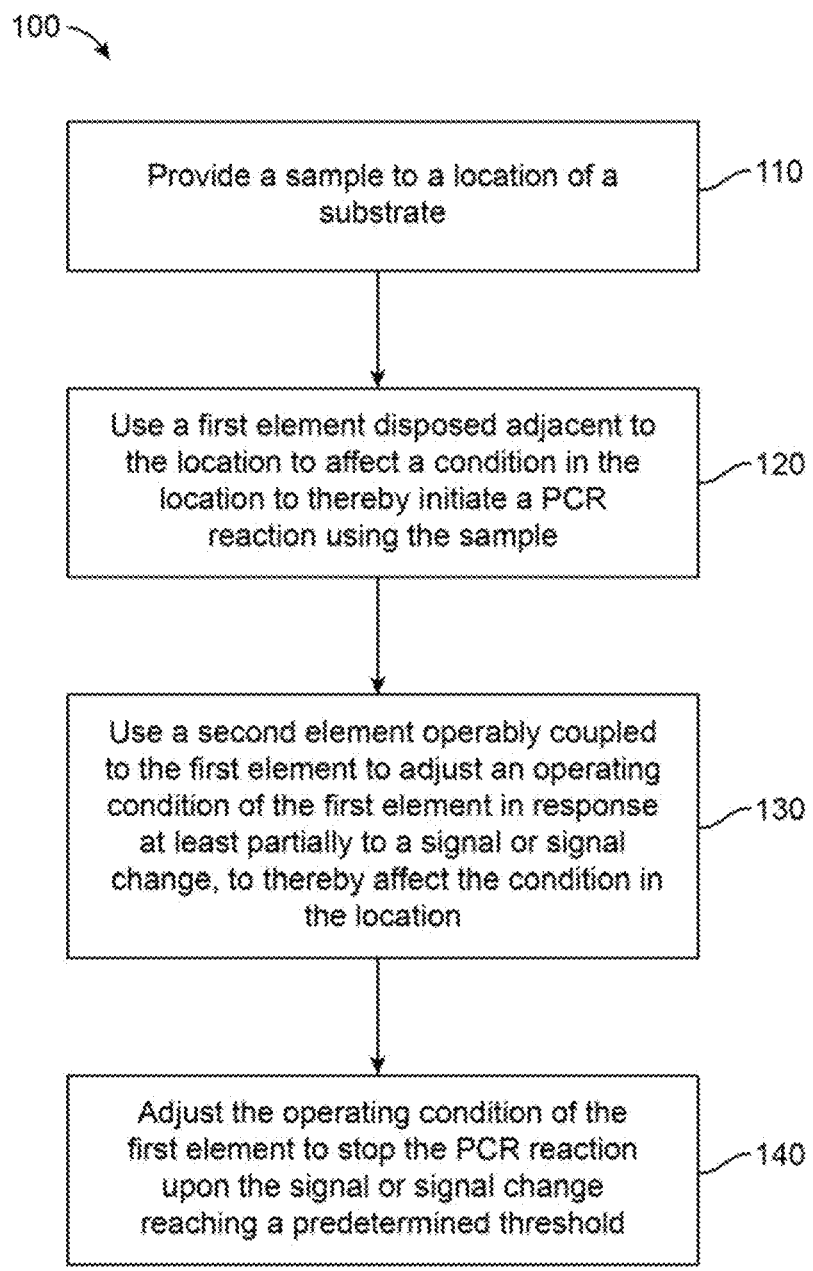
FIG. 1 is a flow chart of a method for performing a polymerase chain reaction (PCR) analysis of a sample containing or suspected of containing an analyte, according to an embodiment of the present disclosure.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

Certain inventive embodiments herein contemplate numerical ranges. When ranges are present, the ranges include the range endpoints. Additionally, every sub range and value within the range is present as if explicitly written out. The term "about" or "approximately" may mean within an acceptable error range for the particular value, which will depend in part on how the value is measured or determined, e.g., the limitations of the measurement system. For example, "about" may mean within 1 or more than 1 standard deviation, per the practice in the art. Alternatively, "about" may mean a range of up to 20%, up to 10%, up to 5%, or up to 1% of a given value. Where particular values are described in the application and claims, unless otherwise stated the term "about" meaning within an acceptable error range for the particular value may be assumed.

In some cases, a device as described elsewhere herein may comprise one or more chambers. The one or more chambers may be locations as described elsewhere herein. For example, a device can comprise a plurality of locations that are a plurality of chambers.

In another aspect, the present disclosure provides a device. The device may comprise a plurality of chambers configured to contain one or more samples. The device may comprise a plurality of elements disposed adjacent to the plurality of chambers. The plurality of elements may be configured to affect at least one condition within each chamber of the plurality of chambers. The device may comprise at least one additional element disposed adjacent to one or more elements of said plurality of elements. The additional element may be configured to affect at least one condition on the plurality of elements. The device may comprise at least one optical system configured to measure a presence or absence of a signal from each chamber of the plurality of chambers.

The device may comprise at least about 1, 2, 3, 4, 5, 10, 25, 50, 75, 96, 100, 150, 200, 250, 300, 350, 384, 400, 450, 500, or more chambers. The device may comprise at most about 500, 450, 400, 384, 350, 300, 250, 200, 150, 100, 96, 75, 50, 25, 10, 5, 4, 3, 2, or fewer chambers. The device may comprise a number of chambers as defined by any two of the preceeding values. A chamber may be configured to contain a volume of at least about 0.1, 0.5, 1, 5, 10, 50, 100, 500, 1,000, 5,000, 10,000, or more microliters. A chamber may be configured to contain a volume of at most about 10,000, 5,000, 1,000, 500, 100, 50, 10, 5, 1, 0.5, 0.1, or less microliters. Each chamber of the plurality of chambers may be of a same size. For example, an array of 96 chambers each with the same volume can be used. The chambers of the plurality of chambers may be different sizes. For example, a device can comprise a plurality of smaller chambers and a plurality of larger chambers. The plurality of chambers may be in a 1-dimensional, 2-dimensional, or 3-dimensional array. For example, the plurality of chambers may be configured similar to a 2-dimensional 96 well plate. In some cases, the plurality of chambers can be organized in a strip. For example, a substrate as described elsewhere herein can be a strip. The plurality of chambers may be configured as a series of individual tubes. In some cases, the chamber is at least a portion of a flow cell. For example, a flow cell can be configured such that a portion of the flow cell is adjacent to the element as described elsewhere herein. The chamber may be at least a portion of a chip. For example, a chip can comprise a plurality of chambers.

The plurality of chambers may be configured to each contain at least about 1, 2, 3, 4, 5, 6, 7, 8, 9, 10, or more samples. For example, a single chamber can be configured with dividers to contain 2 samples within the chamber. The plurality of chambers may be configured to each contain at most about 10, 9, 8, 7, 6, 5, 4, 3, 2, or 1 sample. The plurality of chambers may be collectively configured to contain at least about 1, 5, 10, 25, 50, 75, 100, or more samples. For example, an array of 96 chambers can be configured to contain 96 samples. The plurality of chambers may be collectively configured to contain at most about 100, 75, 50, 25, 10, 5, or less samples. Each chamber of the plurality of chambers may be configured to contain a different sample.

A chamber may be in the form of a well. For example, the chamber can be a cylinder with one open and one closed end. A chamber may comprise one or more of polymers (e.g., plastics, polyethylene, polytetrafluoroethylene, etc.), metals (e.g., pure metals, alloys, etc.), oxides (e.g., glasses, insulative oxides, etc.), semiconductors (e.g., silicon, etc.), or the like, or any combination thereof. A chamber may be configured to not react with a material (e.g., a sample, a reagent, etc.) deposited within the chamber. For example, an iron chamber can be lined with stainless steel to reduce a reaction with a water solvent. In another example, a polyethylene chamber can be lined with polytetrafluoroethylene to protect the chamber for harsh reagents.

The device may comprise a plurality of elements disposed adjacent to the plurality of chambers. The plurality of elements may be in contact with the plurality of chambers. The plurality of elements may be in thermal contact with the plurality of chambers. For example, the plurality of elements can be connected to the plurality of chambers via a plurality of thermal transfer pads.

The plurality of elements may be configured to affect at least one condition within each chamber of the plurality of chambers. The at least one condition may be a temperature, a magnetic field, an optical condition, or the like, or any combination thereof. The condition may be a condition of an individual chamber. For example, the temperature of a first chamber can be held at a different temperature from a second chamber. Each chamber of the plurality of chambers may be maintained at a temperature of at least about 0.1, 0.2, 0.3, 0.4, 0.5, 0.6, 0.7, 0.8, 0.9, 1, 2, 3, 4, 5, 6, 7, 8, 9, 10, or more degrees Celsius from a set temperature for each chamber. Each chamber of the plurality of chambers may be maintained at a temperature of at most about 10, 9, 8, 7, 6, 5, 4, 3, 2, 1, 0.9, 0.8, 0.7, 0.6, 0.5, 0.4, 0.3, 0.2, 0.1, or less degrees Celsius from a set temperature for each chamber. Each chamber of the plurality of chambers may be maintained at a temperature range as defined by any two of the preceeding values. For example, each chamber can be maintained at a temperature in a range from 0.5 to 1 degree Celsius from a set point of each chamber. Each set point may be the same for each chamber. For example, all chambers can be maintained at 50 degrees Celsius. Different chambers may have different set points. For example, a first set of chambers can be maintained at 95 degrees Celsius while a second set of chambers can be maintained at −15 degrees Celsius. The device may be configured to temperature cycle a first subset of the plurality of chambers while maintaining a second subset of the plurality of chambers at a constant temperature. For example, a PCR reaction can be performed in a plurality of chambers. In this example, once a fluorescence signal from a chamber reaches a predetermined level, the PCR reaction in that chamber can be halted by maintaining the chamber at a low temperature. In this example, other chambers can continue to be cycled to continue the PCR reactions occurring in those chambers.

The device may be configured to generate a condition gradient across the plurality of chambers. For example, the device can be configured to generate a temperature gradient across the plurality of chambers. In this example, the optimal temperature for a reaction can be determined by investigating the reaction progress across the temperature gradient. In another example, gradient of reagent concentrations can be generated. A melt-curve analysis may be performed by the device across the plurality of chambers.

The plurality of elements may comprise a plurality of heating and/or cooling elements. The heating and/or cooling elements may be separate elements. For example, a heating element and a cooling element can be adjacent to one another in contact with a chamber. The heating and/or cooling elements may be a same element. For example, a combined heating and cooling element can be disposed adjacent to the chamber. In this example, a thermoelectric element can be used as both a heating element and a cooling element. The heating element may comprise a resistive heater, an inductive heater, a thermoelectric heater, or the like, or any combination thereof. The cooling element may comprise an evaporative cooler, a compressive cooler, a thermoelectric cooler, or the like, or any combination thereof.

The at least one additional element may be disposed adjacent to one or more elements of the plurality of elements. The at least one additional element may be disposed adjacent to all of the plurality of elements. For example, the plurality of elements can each be in contact with the additional element. The additional element may comprise one or more additional heating and/or cooling elements. The one or more additional heating and/or cooling elements may be as described elsewhere herein. For example, the additional element may comprise a large thermoelectric element in thermal communication with a plurality of thermoelectric elements. The at least one condition on the plurality of elements may be a condition as described elsewhere herein. For example, the at least one additional element can be configured to affect a temperature of the plurality of elements. In this example, a thermoelectric cooler can be used to reduce the hot side temperature and thereby increase the efficiency of a plurality of thermoelectric elements which in turn can individually control the temperature of the chambers. The at least one additional element may comprise at least about 1, 2, 3, 4, 5, 6, 7, 8, 9, 10, or more additional elements. The at least one additional element may comprise at most about 10, 9, 8, 7, 6, 5, 4, 2, or less additional elements.

The optical system may comprise one or more excitation sources. Examples of excitation sources include, but are not limited to, a laser (e.g., a single wavelength laser, a supercontinuum laser, etc.), an incoherent light source (e.g., a light emitting diode, an incandescent light source, etc.), or the like, or any combination thereof. The optical system may comprise one or more detectors. Examples of detectors include, but are not limited to, a zero-dimensional (0D) detectors (e.g., a photodiode), a silicon photomultiplier (SiPM), a one-dimensional (1D) detectors (e.g., a strip detector), a two-dimensional (2D) detectors (e.g., an array detector), a film detector (e.g., a detector using silver halide crystals on a film), a phosphor plate detector (e.g., a plate of downshifting or down-converting phosphor), a semiconductor detector (e.g., a semiconductor charge coupled device (CCD), a complementary metal oxide semiconductor (CMOS) device), or the like, or any combination thereof. The optical system may be configured to measure the presence or absence of the signal from each chamber of the plurality of chambers individually. For example, the optical system can collectively excite the plurality of chambers and individually read the signal from each chamber. In another example, the optical system can individually excite and read the signals from each chamber.

The plurality of elements may comprise a plurality of thermoelectric heating, thermoelectric cooling, or combined thermoelectric heating and cooling elements. For example, a thermoelectric heating element can become a thermoelectric cooling element with a reversal of a current polarity across the thermoelectric element. The at least one additional element may comprise at least one thermoelectric heater, thermoelectric cooler, or combined thermoelectric heater and cooler. The device may comprise one or more heat pipes configured to reduce thermal crosstalk between the plurality of chambers. For example, the heat pipes can be placed in between the chambers to improve thermal isolation between the chambers. The heat pipes may be configured to, or be in thermal contact with an element configured to, dissipate excess heat and/or add heat to remove a heat deficit.

In another aspect, the present disclosure provides a method for performing a polymerase chain reaction (PCR) analysis of a sample containing or suspected of containing an analyte. The method may comprise providing the sample to a first chamber of a device comprising one or more chambers configured to contain the sample. The one or more chambers may be configured to have individually controllable conditions. A PCR reaction may be initiated using the sample. The PCR reaction may generate a signal indicative of a presence or absence of the analyte. The PCR reaction may be monitored using the signal. The PCR reaction may be stopped after a predetermined amount of signal is generated by the PCR reaction within the chamber.

FIG. 1 is a flow chart of a method 100 for performing a polymerase chain reaction (PCR) analysis of a sample containing or suspected of containing an analyte, according to an embodiment of the present disclosure. The method may comprise providing the sample to a location of a substrate (110). The location may have a volume configured to retain the sample and permit the sample to be subjected to a condition for the PCR analysis. The device may be as described elsewhere herein. For example, the one or more chambers may be configured to have individually controllable conditions. In another example, the signal can comprise an optical signal.

A sample may be a material that may comprise an analyte. The sample may be suspected of comprising the analyte. A sample may be solid matter (e.g., biological tissue) or may be a fluid (e.g., a biological fluid). In general, a biological fluid can include any fluid associated with living organisms. Non-limiting examples of a samples include blood (or components of blood—e.g., white blood cells, red blood cells, platelets) obtained from any anatomical location (e.g., tissue, circulatory system, bone marrow) of a subject, cells obtained from any anatomical location of a subject, skin, heart, lung, kidney, breath, bone marrow, stool, semen, vaginal fluid, interstitial fluids derived from tumorous tissue, breast, pancreas, cerebral spinal fluid, tissue, throat swab, biopsy, placental fluid, amniotic fluid, liver, muscle, smooth muscle, bladder, gall bladder, colon, intestine, brain, cavity fluids, sputum, pus, micropiota, meconium, breast milk, prostate, esophagus, thyroid, serum, saliva, urine, gastric and digestive fluid, tears, ocular fluids, sweat, mucus, earwax, oil, glandular secretions, spinal fluid, hair, fingernails, skin cells, plasma, nasal swab or nasopharyngeal wash, spinal fluid, cord blood, emphatic fluids, and/or other excretions or body tissues. A sample may be a cell-free sample. Such cell-free sample may include DNA and/or RNA. The analyte may be a nucleic acid molecule, a protein (e.g., an antibody), an antigen, a chemical (e.g., a toxin), a metal ion (e.g., a heavy metal ion), or the like. For example, the analyte can be a nucleic acid molecule of a virus.

The method 100 may comprise using a first element disposed adjacent to the location to affect the condition in the location to thereby initiate the PCR reaction using the sample (120). The PCR reaction may generate a signal or signal change which is indicative of a property associated with the analyte. The PCR reaction may generate a signal indicative of a presence or absence of the analyte. The PCR reaction may comprise Allele-specific PCR, Assembly PCR, Polymerase Cycling Assembly (PCA), Asymmetric PCR, Convective PCR, Dial-out PCR, Digital PCR (dPCR), Helicase-dependent amplification, Hot start PCR, In silico PCR, Intersequence-specific PCR, Inverse PCR, Ligation-mediated PCR, Methylation-specific PCR, Miniprimer PCR, Multiplex ligation-dependent probe amplification, MLPA, Multiplex-PCR, Nanoparticle-Assisted PCR (nanoPCR), Nested PCR, Overlap-extension PCR, Splicing by overlap extension (SOEing), PAN-AC, quantitative PCR, real-time Quantitative PCR, Reverse Complement PCR, Reverse Transcription PCR (RT-PCR), Rapid Amplification of cDNA Ends, RNase H-dependent PCR, Single Specific Primer-PCR, Solid Phase PCR, Suicide PCR, Thermal asymmetric interlaced PCR (TAIL-PCR), Touchdown PCR, Step-down PCR, Universal Fast Walking, or the like. The signal may comprise an optical signal, an electrical signal, a physical signal, or the like, or any combination thereof. The optical signal may comprise an absorption signal (e.g., an absorption intensity, an absorption peak wavelength), a fluorescence signal (e.g., a fluorescence intensity, a fluorescence wavelength, a fluorescence lifetime), a plasmonic property, or the like, or any combination thereof. The electrical signal may comprise resistance, impedance, capacitance, or the like, a change thereof, or any combination thereof. The physical signal may comprise a physical state of the sample. For example, a physical signal can be a melting point of the sample.

The method 100 may comprise using a second element operably coupled to the first element to adjust an operating condition of the first element at least partially in response to the signal or signal change, to thereby affect the condition in the location (130). Since the signal can be dependent on the amount of analyte within the sample, the device can use the amount of signal as a proxy for how far the reaction has progressed. As such, instead of using an arbitrary number of cycles to determine the reaction progress, the signal can instead be used as a quantitative measure. The monitoring may comprise real-time monitoring (e.g., reading the signal in real-time as the reaction progresses), fixed-interval monitoring (e.g., reading the signal at predetermined times), or the like, or any combination thereof. The method 100 may comprise adjusting the operating condition of the first element to stop the PCR reaction upon said signal or signal change reaching a predetermined threshold (140). For example, once a predetermined amount of fluorescent signal is generated in a chamber, the PCR reaction can be stopped by reducing the temperature. Examples of operating conditions include, but are not limited to, temperature, agitation (e.g., stirring, shaking, etc.), presence or absence of light, presence or absence of chemical compounds (e.g., additional reagents, gasses, etc.), or the like, or any combination thereof. For example, an operating condition can be a temperature of the reaction, and a change in the operating condition can be a change in the temperature. In another example, an operating condition can be a presence of light energy, and the change in the operating condition can be turning off the light.

A second chamber of the device may comprise a second sample. For example, the first chamber can contain a sample from a first subject, and the second chamber can comprise a sample from a second subject. In another example, the first chamber can contain a first sample from a subject, and the second chamber can contain a second sample from the same subject. The second chamber may continue a second PCR reaction within the second chamber after the stopping of the PCR reaction in the first chamber. The conditions within the second chamber may be controlled separately from the conditions in the first chamber. As such, the reaction in the second chamber can be independent from the reaction in the first chamber. Since the reactions can be independently controlled and monitored, once a reaction is determined to be complete, it can be halted without impacting adjacent reactions. For example, when a reaction reaches a predetermined amount of signal indicative of a presence of an analyte, the reaction can be halted and kept under appropriate conditions to later retrieve the products of the reaction.

The method 100 may not comprise pre-normalization. The method can be performed on a sample that does not comprise an internal standard. The method can be performed on a sample without quantifying a non-analyte target within the sample. For example, the method can be performed to quantify a viral nucleic acid analyte without also amplifying a human gene control. The method 100 may not comprise pre-quantification. The method may not comprise determining an amount of analyte within the sample. For example, the method can be performed on a sample with an unknown amount of nucleic acid molecules present in the sample. By performing the method on a sample that is not normalized and/or pre-quantified, the time taken to process the sample can be reduced. Additionally, the complexity and cost associated with processing the sample can be reduced as well. This may be contrary to other sample analysis techniques, which may require pre-normalization or pre-quantification to maintain high accuracy. The method 100 may maintain a high accuracy, sensitivity, and/or specificity without these operations. The presence or absence of the analyte may be determined with a accuracy, sensitivity, and/or specificity of at least about 10%, 20%, 30%, 40%, 50%, 60%, 70%, 80%, 85%, 90%, 91%, 92%, 93%, 94%, 95%, 96%, 97%, 98%, 99%, 99.5%, 99.9% or more. The presence or absence of the analyte may be determined at an accuracy, sensitivity, and/or specificity of at most about 99.9%, 99.5%, 99%, 98%, 97%, 96%, 95%, 94%, 93%, 92%, 91%, 85%, 80%, 70%, 60%, 50%, 40%, 30%, 20%, 10%, or less.

A subject may be an animal, such as a mammal. A subject may be a human or non-human mammal. A subject may be a plant. A subject may be afflicted with a disease or suspected of being afflicted with or having a disease. The subject may not be suspected of being afflicted with or having the disease. The subject may be symptomatic. Alternatively, the subject may be asymptomatic. In some cases, the subject may be treated to alleviate the symptoms of the disease or cure the subject of the disease. A subject may be a patient undergoing treatment by a healthcare provider, such as a doctor. The subject may be a healthcare provider. The subject may be a student, a teacher, a long-term caregiver (e.g., a nursing home employee), a prison guard, or others who work and/or live in close proximity to others.

Figure 2:
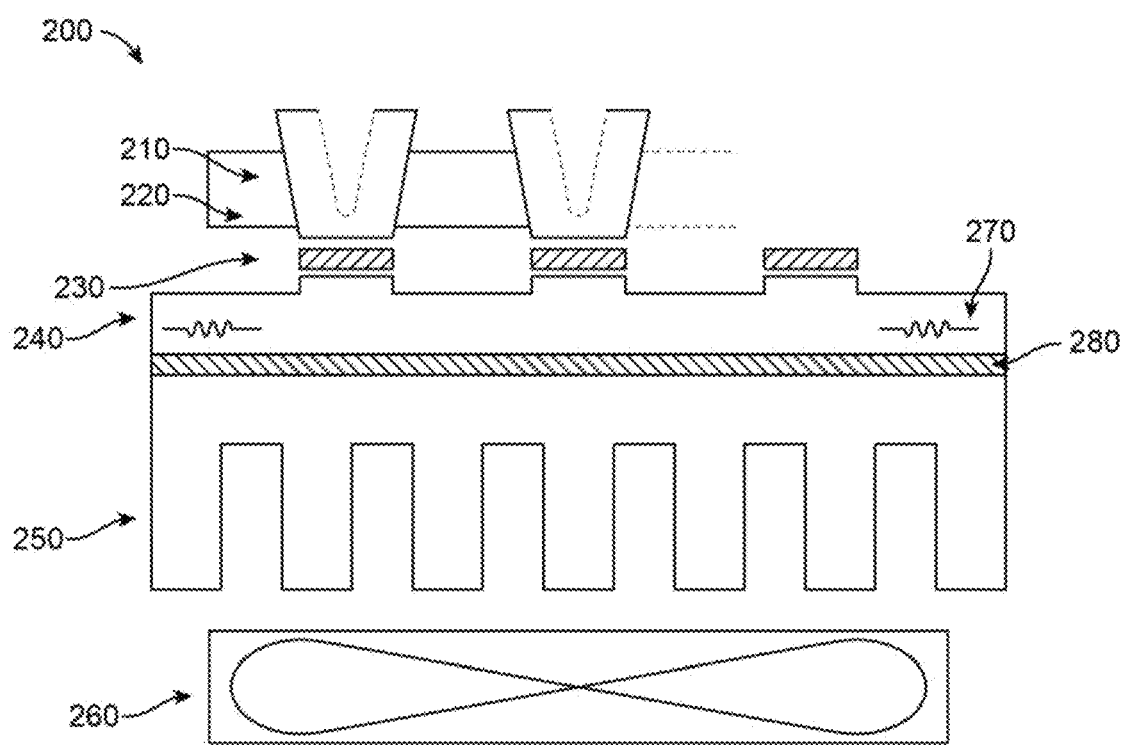
FIG. 2 is a schematic of a device, according to an embodiment.

FIG. 2 is a schematic of a device 200, according to an embodiment. The device 200 may comprise one or more chambers 210. In this example, the chambers can be wells configured to be fluidically accessible from the top of the chamber. The chamber can additionally be configured to be optically accessible. For example, a camera positioned facing the top of the chamber can read an optical signal originating from the chamber. Each chamber may comprise insulation 220. The insulation may be configured to decrease thermal transfer between the chambers of the plurality of chambers. For example, when a first chamber is under heating conditions and a second chamber is under cooling conditions, the insulation can reduce the heat that leaks from the heated chamber into the cooled chamber, improving efficiency and accuracy. The insulation 220 may comprise one or more of a low thermal conductivity materials. The insulation may comprise mineral wools (e.g., fiberglass), natural fibers (e.g., cellulose), polymers (e.g., polystyrene, polyurethane, etc.), or any combination thereof. The insulation may comprise one or more heat pipes. The one or more heat pipes may be configured to provide transport of heat to or from the chambers. For example, the heat pipe can remove excess heat away from the chambers. The heat pipe may comprise a solid metal pipe (e.g., a copper wire), a phase change heat pipe (e.g., a copper tube filled with a phase change cooler), or the like, or any combination thereof. In some cases, each chamber can have an associated temperature reader (e.g., thermometer, thermocouple, etc.). The temperature reader can be configured to read a temperature of the chamber and provide the temperature to a central controller. This can enable individual, real-time control of the temperature of each chamber of the plurality of chambers.

The device may comprise one or more elements 230. The device may comprise one element for each chamber of the device as shown in FIG. 2. The device may comprise a plurality of elements for each chamber. The elements may be as described elsewhere herein. For example, the elements may be thermoelectric elements. The thermoelectric elements may be configured to individually control the temperature within each chamber of the device. For example, a thermoelectric element positioned below a chamber can heat and cool that chamber. The thermoelectric elements may be connected to an optional thermoelectric back plate 240 comprising an optional heater 270. The thermoelectric back plate may be configured to equalize the temperature for the elements 230 to improve efficiency. For example, if the chambers are being heated, the backs of the thermoelectric elements can get cold. In this example, the heater 270 can provide heat to the thermoelectric back plate to regulate the back side temperatures of the thermoelectric elements. The thermoelectric back plate can be in thermal contact with a heatsink 250 via an optional graphite pad 280. The graphite pad may be configured to aid in heat conduction between the thermoelectric back plate and the heatsink. For example, the graphite pad can fill defects in the thermoelectric back plate and the heatsink to provide a better thermal conduction. The heatsink may comprise a metal heatsink (e.g., copper, aluminum, etc.), a polymer heatsink, a graphite heatsink, or the like, or any combination thereof. The heatsink may be cooled by a fan 260. The fan can circulate air around the heatsink to aid in the dissipation of heat from the device.

Figure 15A:
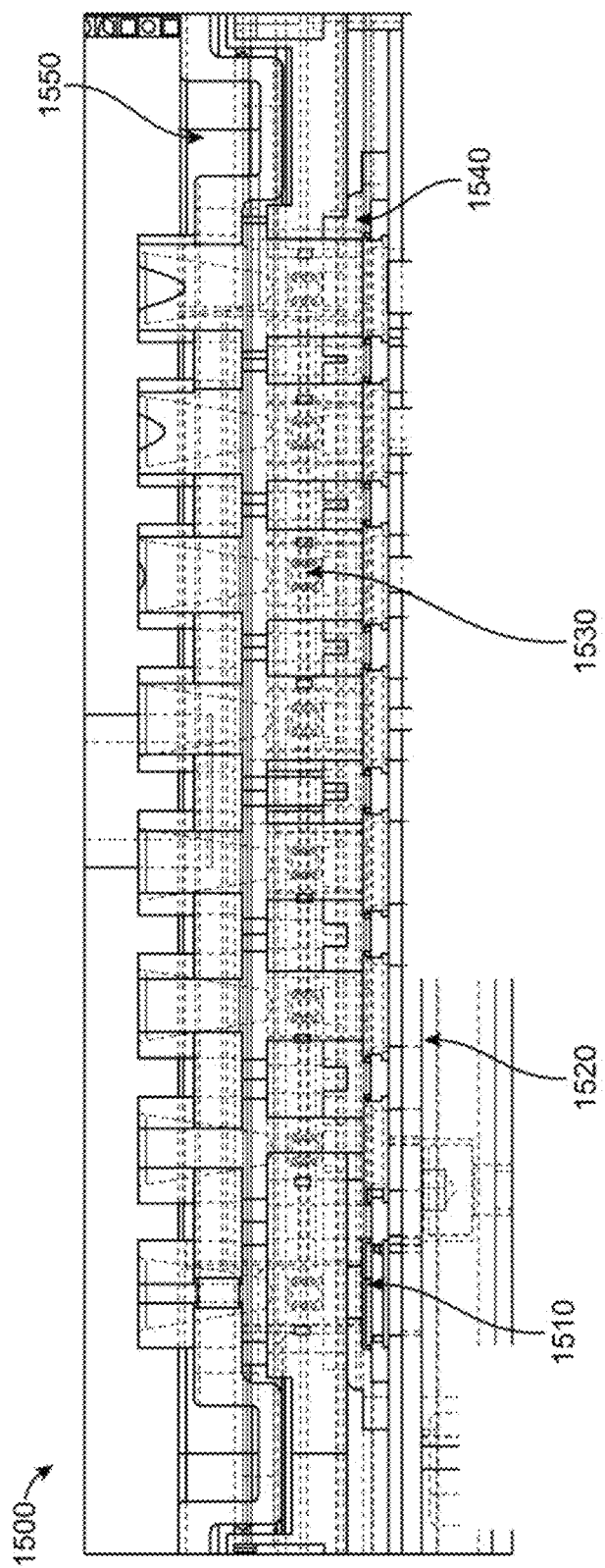
FIGS. 15A-15C are examples of a pillar design, according to some embodiments.
Figure 15B:
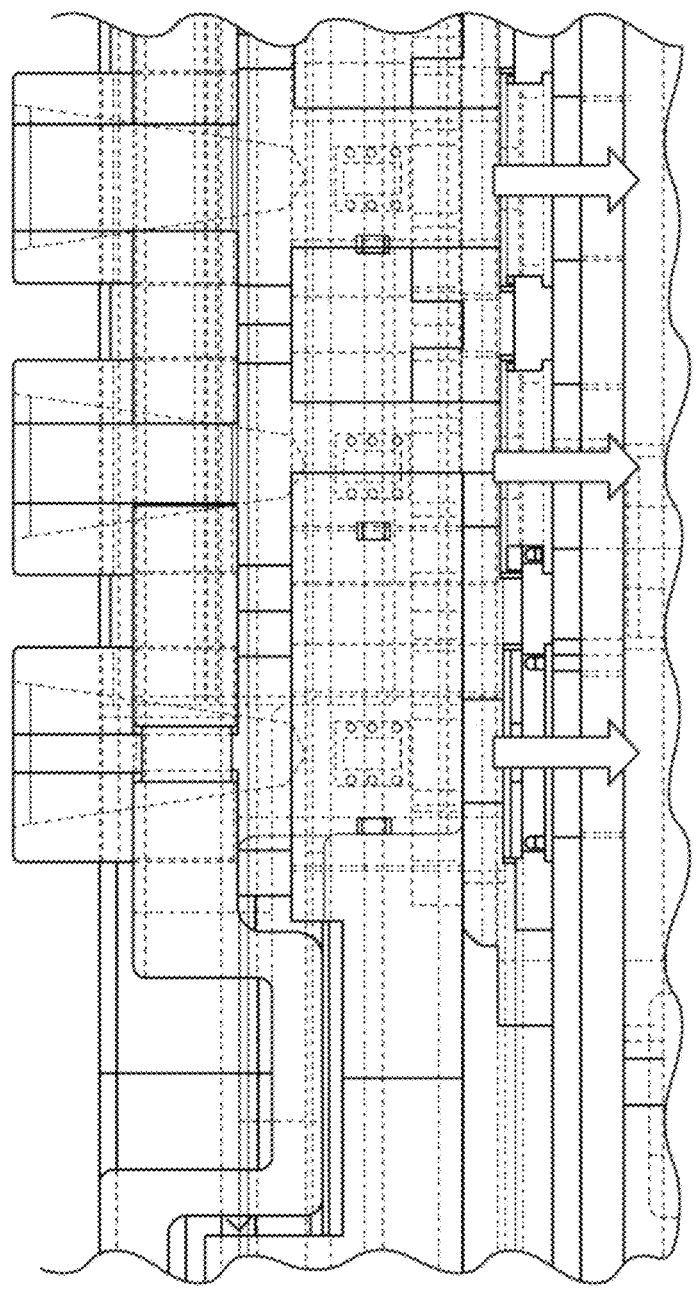
Figure 15C:
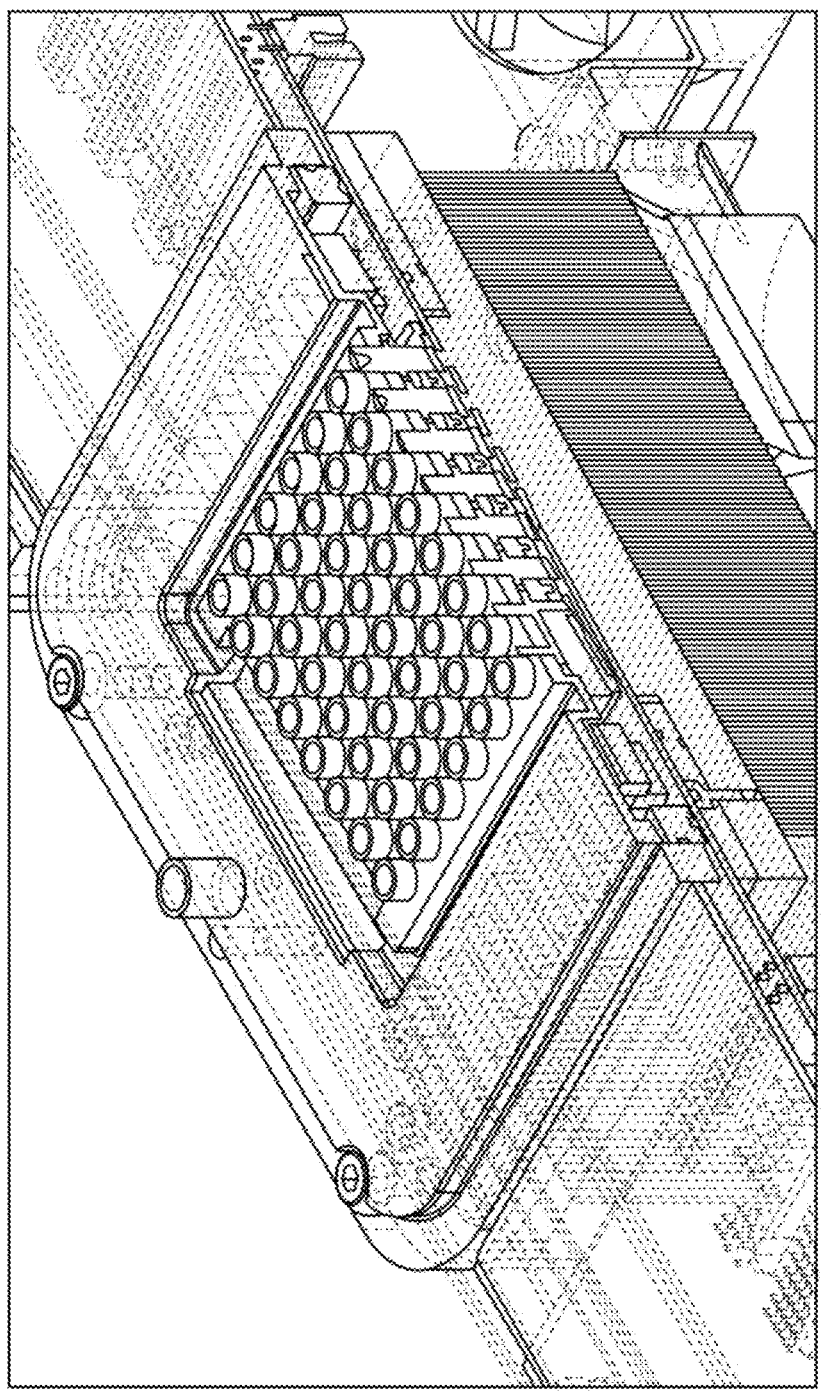

In some cases, the heatsink can comprise a pillar design. FIGS. 15A-15C are examples of a pillar design, according to some embodiments. The pillar design may be configured to facilitate heat transfer between the thermoelectric elements and a larger heatsink (e.g., a plurality of fins). The pillar design may be configured to reduce crosstalk between the individual chambers of the device. For example, the pillars can be configured to direct heat through the pillars, but the space between the pillars can reduce crosstalk between the pillars. Each chamber may be in thermal contact with a different pillar. In some cases, each pillar may not have a direct connection between the other pillars. In some cases, there may not be a direct connection between each of the chambers. For example, the chambers may be in physical contact with a thermally insulating material, but not in contact with a thermally conductive material placed between the chambers. In FIG. 15A, the device 1500 may comprise one or more elements 1510 (e.g., thermoelectric elements as described elsewhere herein) and one or more pillars (e.g., insulating pillars) 1520. The pillars can be configured to thermally isolate the plurality of chambers while enabling movement of heat as described elsewhere herein. The device may further comprise one or more temperature sensors 1530 as described elsewhere herein. A retaining clip 1540 can be configured to retain the plurality of elements, while a retaining plate 1550 can be configured to retain the plurality of chambers.

Figure 3:
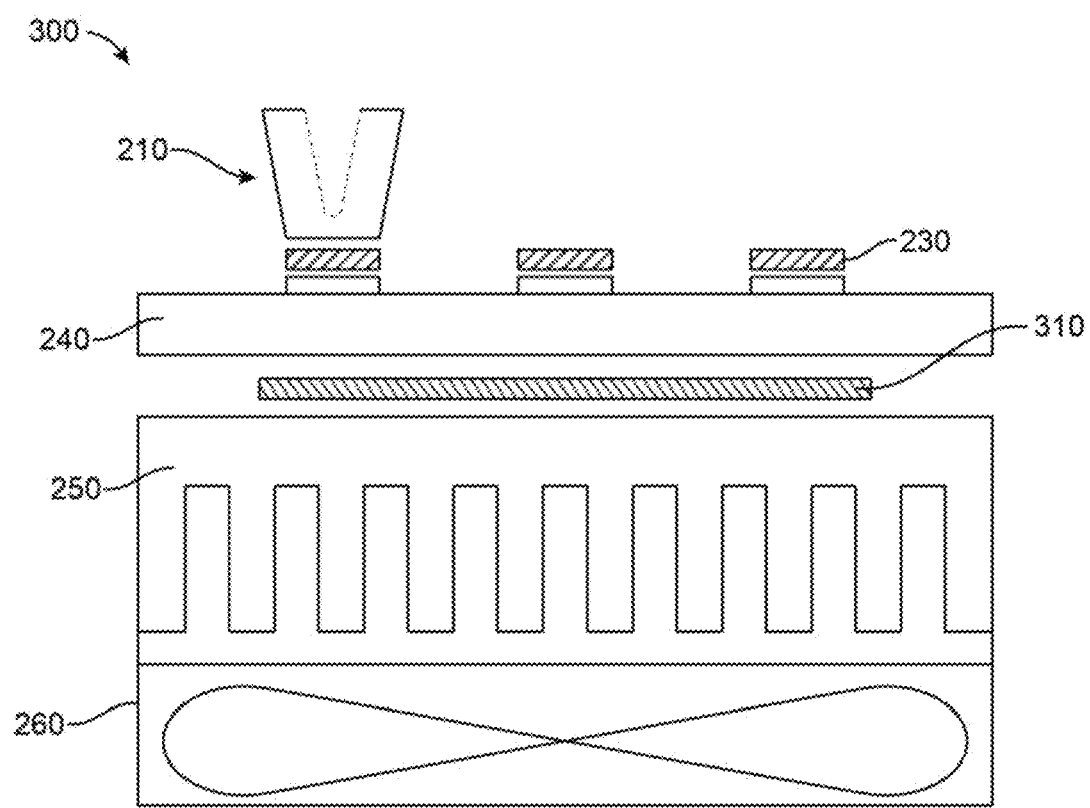
FIG. 3 is a schematic of a device, according to an embodiment.

FIG. 3 is a schematic of a device 300, according to an embodiment. The device 300 may be similar to the device 200 of FIG. 2 but for the addition of an additional element 310 disposed adjacent to the thermoelectric back plate 240. The additional element may be one or more additional thermoelectric elements. The one or more additional elements can be configured to control a condition (e.g., a temperature) of the one or more elements. For example, a second thermoelectric cooler can cool the hot sides of a plurality of thermoelectric coolers. Including the one or more additional elements can improve the performance of the one or more elements by removing waste heat from the one or more elements. Additionally, such additional elements can provide a dynamic control of the conditions for the one or more elements. For example, a first thermoelectric element can switch between heating and cooling a chamber. In this example, an additional thermoelectric element can switch between cooling and heating the first thermoelectric element.

Figure 16A:
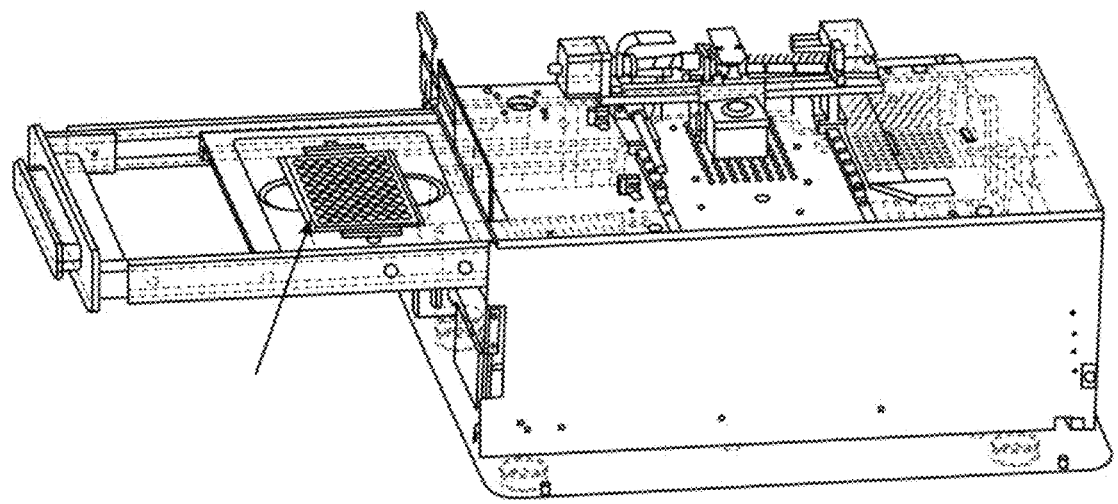
FIGS. 16A-16B show different views of an example of a device, according to some embodiments.
Figure 16B:
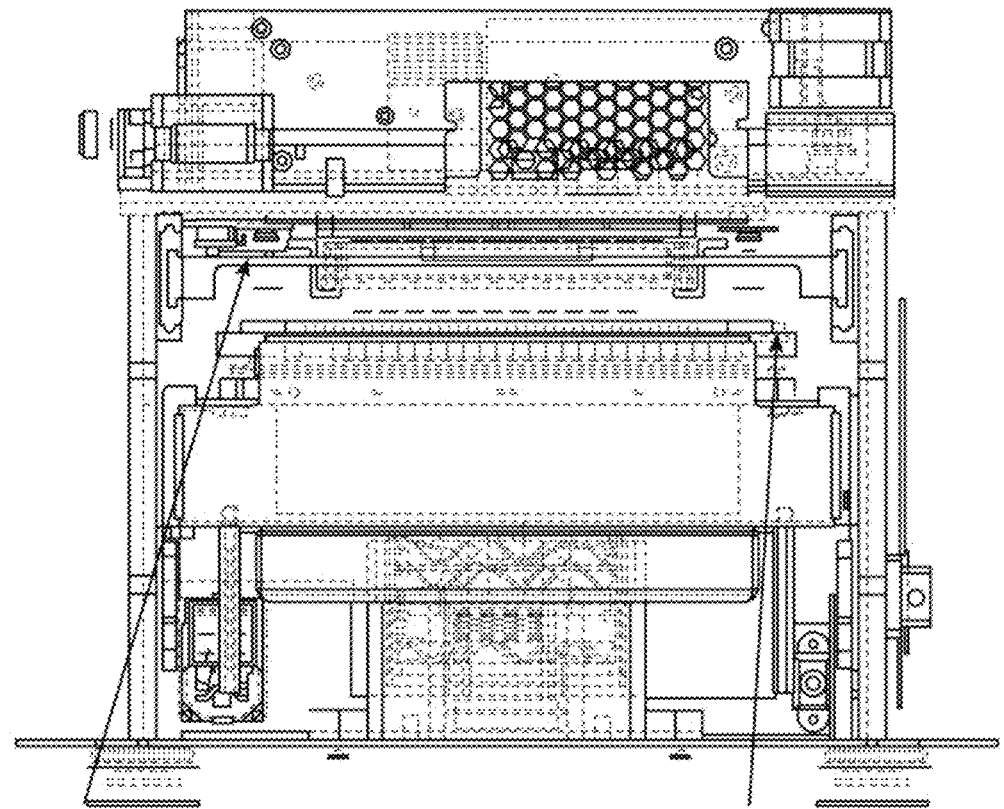

FIGS. 16A-16B show different views of an example of a device, according to some embodiments. The device may be as described elsewhere herein. In some cases, a microwell plate can be placed within a plate holder. The plate holder may be configured to move the microwell plate into the device (e.g., into contact with a thermal elements). The movement of the plate holder may be automated (e.g., actuated by motors within the device). The movement of the plate holder may be manual (e.g., a user can slide the plate holder into the device). In some cases, the microwell can, once inserted into the device, be held in a fixed position while a thermal element can be moved to engage with the well plate. For example, a heat pump can be moved vertically to engage with the bottom of the microwell plate. In some cases, the microwell plate can be moved once inserted into the device to engage the microwell plate with a thermal element. For example, the microwell plate can be pressed down to engage with a heat pump. The movement within the device may be effected by, for example, a linear motor, a rotary motor, or the like, or any combination thereof.

Figure 17:
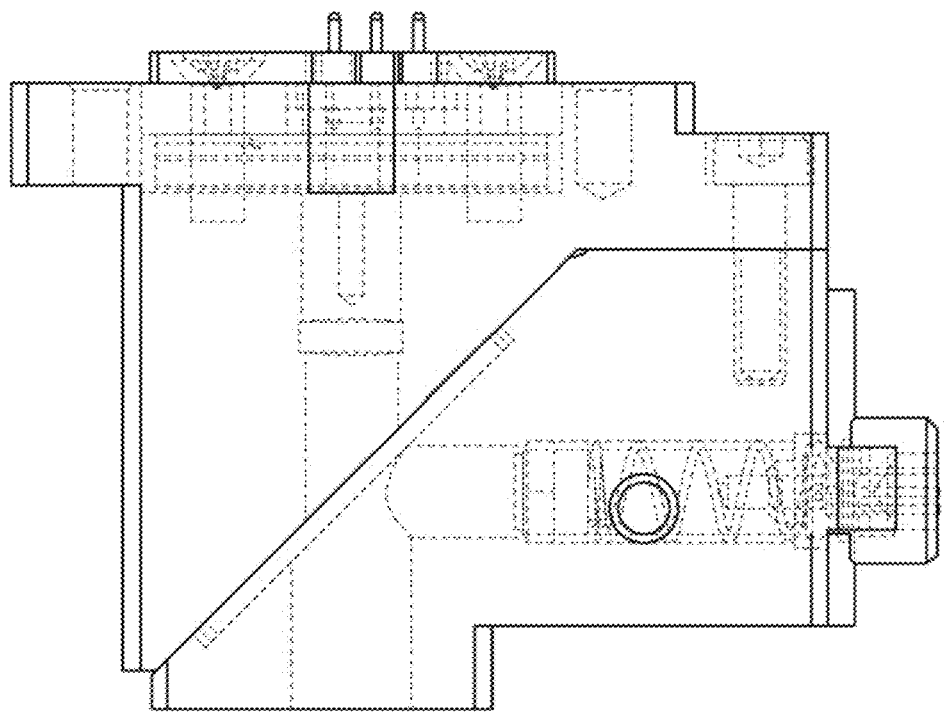
FIG. 17 shows an example of an optics assembly, according to some embodiments.
Figure 18:
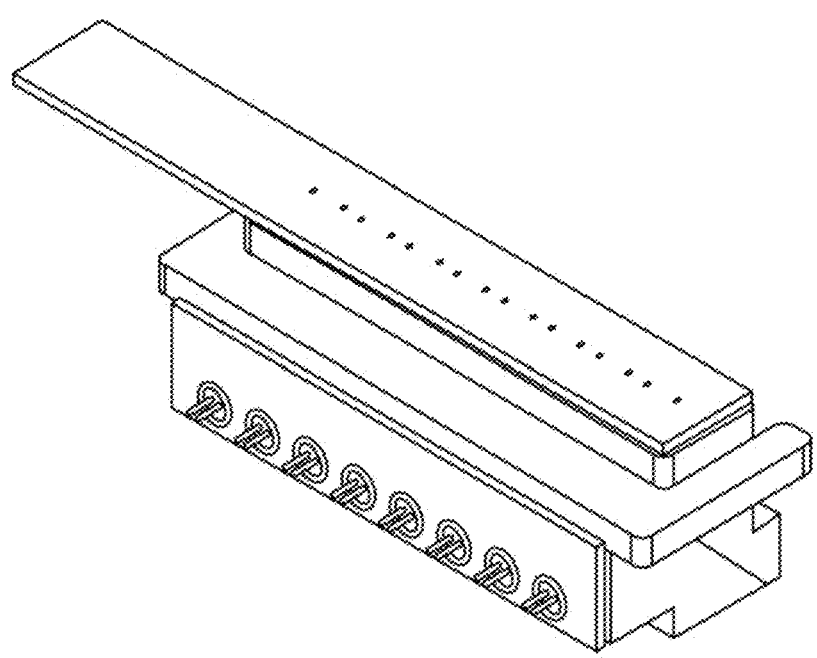
FIG. 18 shows an example of a configuration of a plurality of optical assemblies, according to some embodiments.
Figure 19:
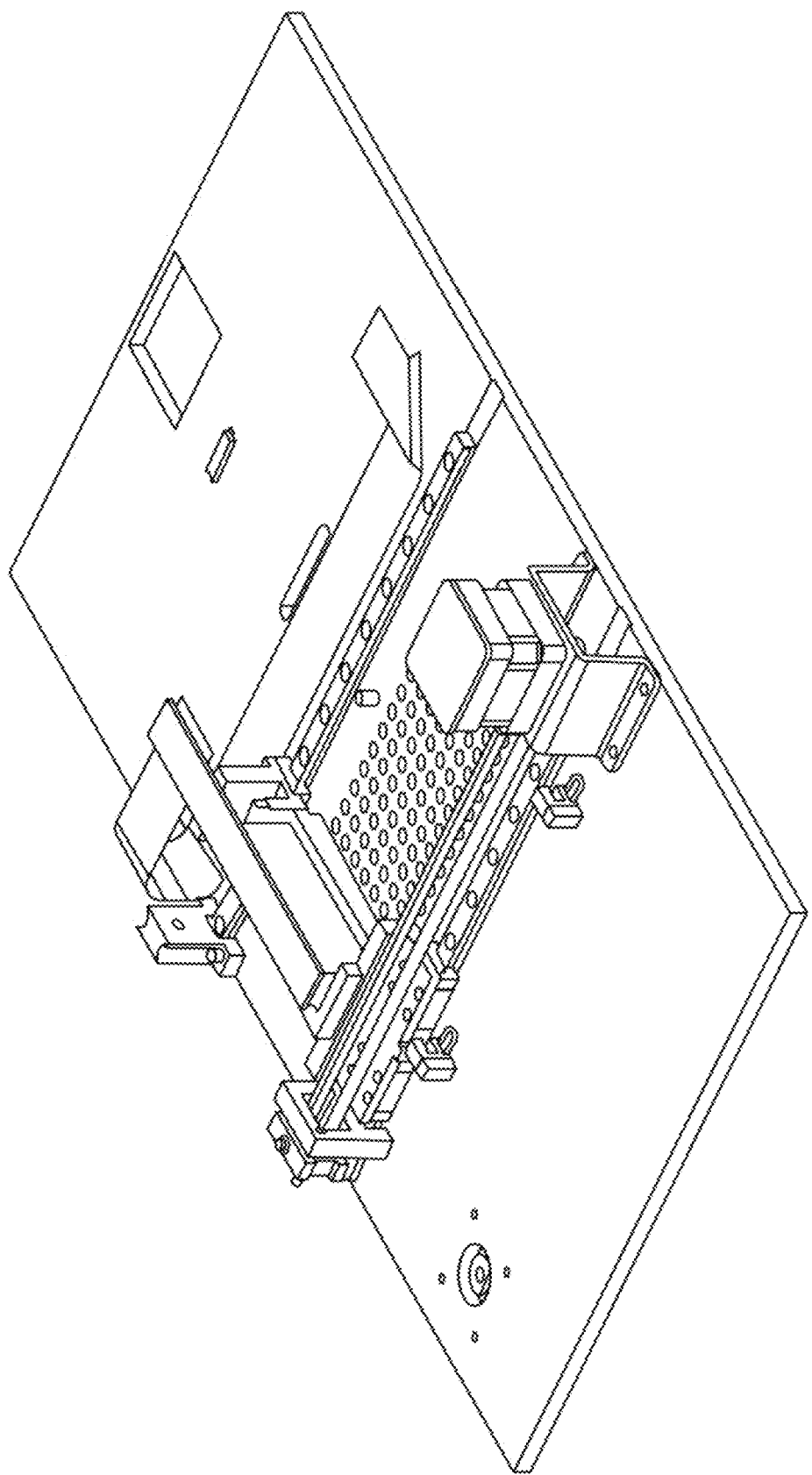
FIG. 19 shows an example of a unit comprising a plurality of optics assemblies positioned adjacent to a plurality of chambers, according to some embodiments.
Figure 20:
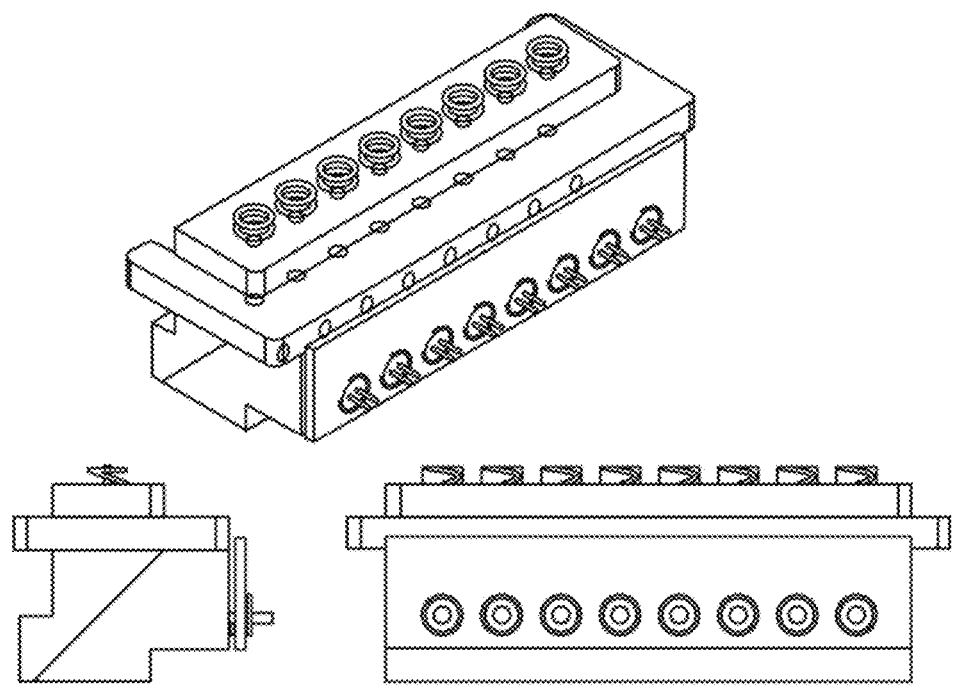
FIG. 20 shows an example unit comprising 8 optics assemblies, according to some embodiments.
Figure 21:
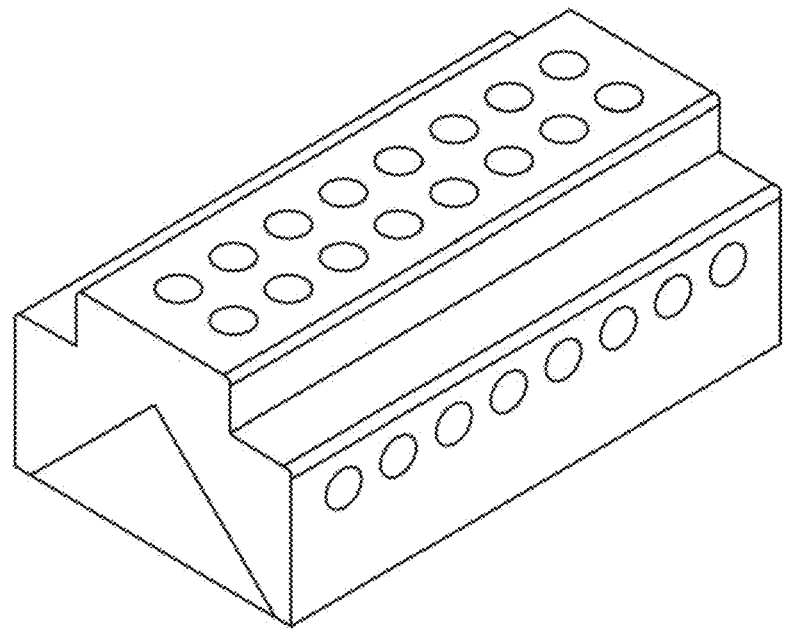
FIG. 21 shows an example unit comprising 16 optics assemblies in a single unit, according to some embodiments.

FIG. 17 shows an example of an optics assembly, according to some embodiments. The optics assembly may be configured to provide optical excitation and/or receive optical emissions from one or more chambers (e.g., wells) of a plate. For example, the optics assembly can be configured to provide an excitation beam from a first optical port into the optics assembly. In some cases, the first optical port can comprise a laser (e.g., a diode laser). In this way, the excitation beam can be generated from within the optics assembly. In some cases, the optics assembly can comprise a dichroic mirror configured to direct the excitation beam from the first optical port to a chamber. The excitation beam can excite a fluorophore within the chamber, and the resultant emission can travel back into the optics assembly, through the dichroic mirror, and be directed to a second optical port and/or a detector module. In some cases, the emission can be removed from the optics assembly by, for example, coupling the emission light into a fiber optic. The removed emission light can then be directed towards a detector. In some cases, the optics assembly can comprise a detector configured to detect the emission light without the emission light being removed from the optics assembly. FIG. 18 shows an example of a configuration of a plurality of optical assemblies, according to some embodiments. In this example, 8 optics assemblies have formed as a single unit, which can be configured to monitor the optical signal from 8 chambers. The plurality of optics assemblies can be configured into a unit comprising at least about 1, 2, 3, 4, 5, 6, 7, 8, 9, 10, 11, 12, 13, 14, 15, 16, 17, 18, 19, 20, or more optics assemblies. The plurality of optics assemblies can be configured into a unit comprising at most about 20, 19, 18, 17, 16, 15, 14, 13, 12, 11, 10, 9, 8, 7, 6, 5, 4, 3, 2, or fewer optics assemblies. For example, FIG. 20 shows an example unit comprising 8 optics assemblies, according to some embodiments. In another example, FIG. 21 shows an example unit comprising 16 optics assemblies in a single unit, according to some embodiments. In some cases, the optics assemblies can be configured on different sides of a unit. In some cases, the optics assemblies can be configured on a same side of a unit (e.g., stacked). The addition of additional optics units may not substantially increase the footprint of the unit while reducing the length of time for a device to collect fluorescent intensities from the chambers of the device. FIG. 19 shows an example of a unit comprising a plurality of optics assemblies positioned adjacent to a plurality of chambers, according to some embodiments. The unit can be configured to move across the plurality of chambers by use of, for example, a stepper motor and a timing belt.

Figure 4A:
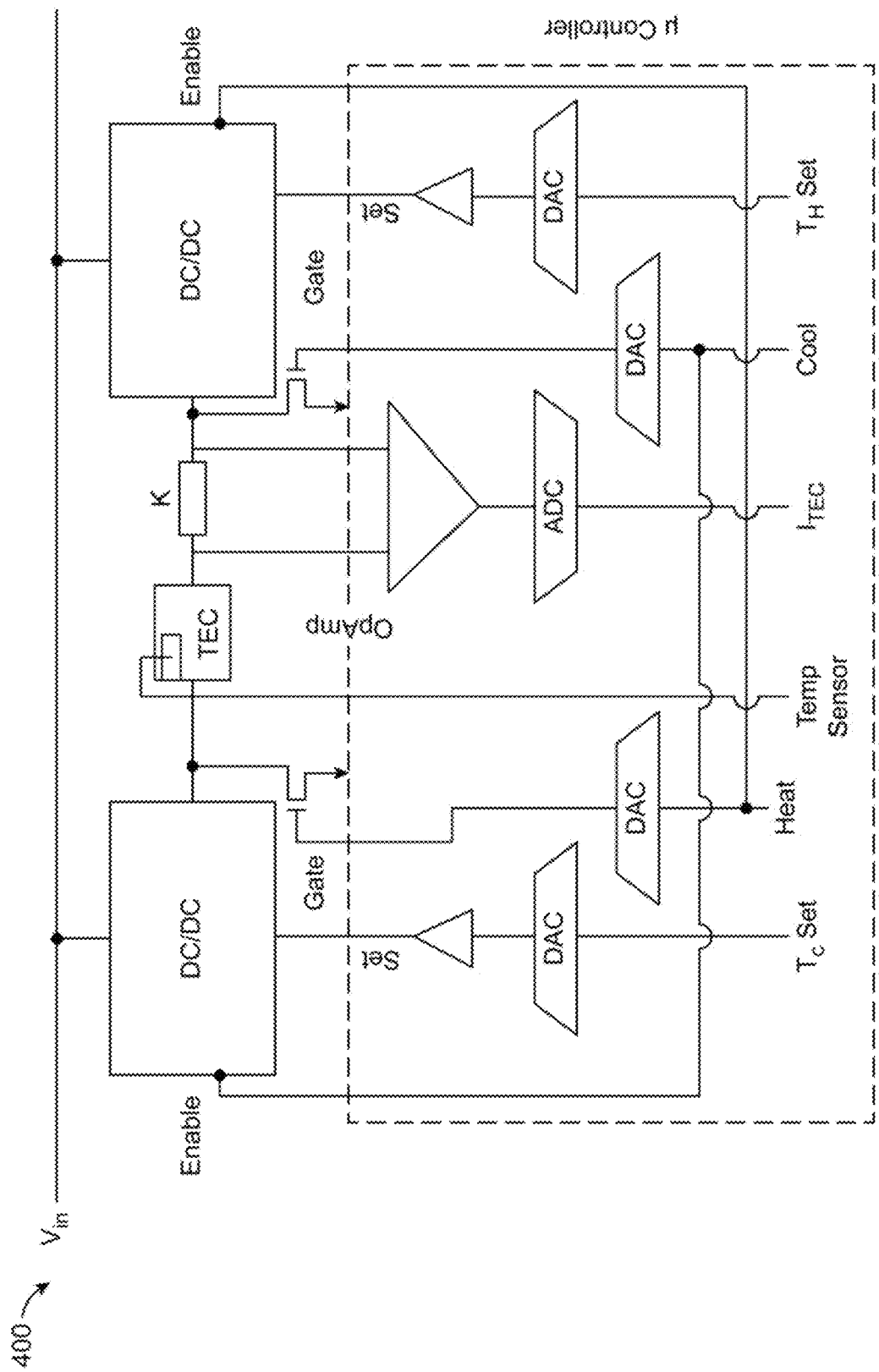
FIG. 4A is a schematic of a thermoelectric control architecture without a current sink capacity, according to an embodiment.
Figure 4B:
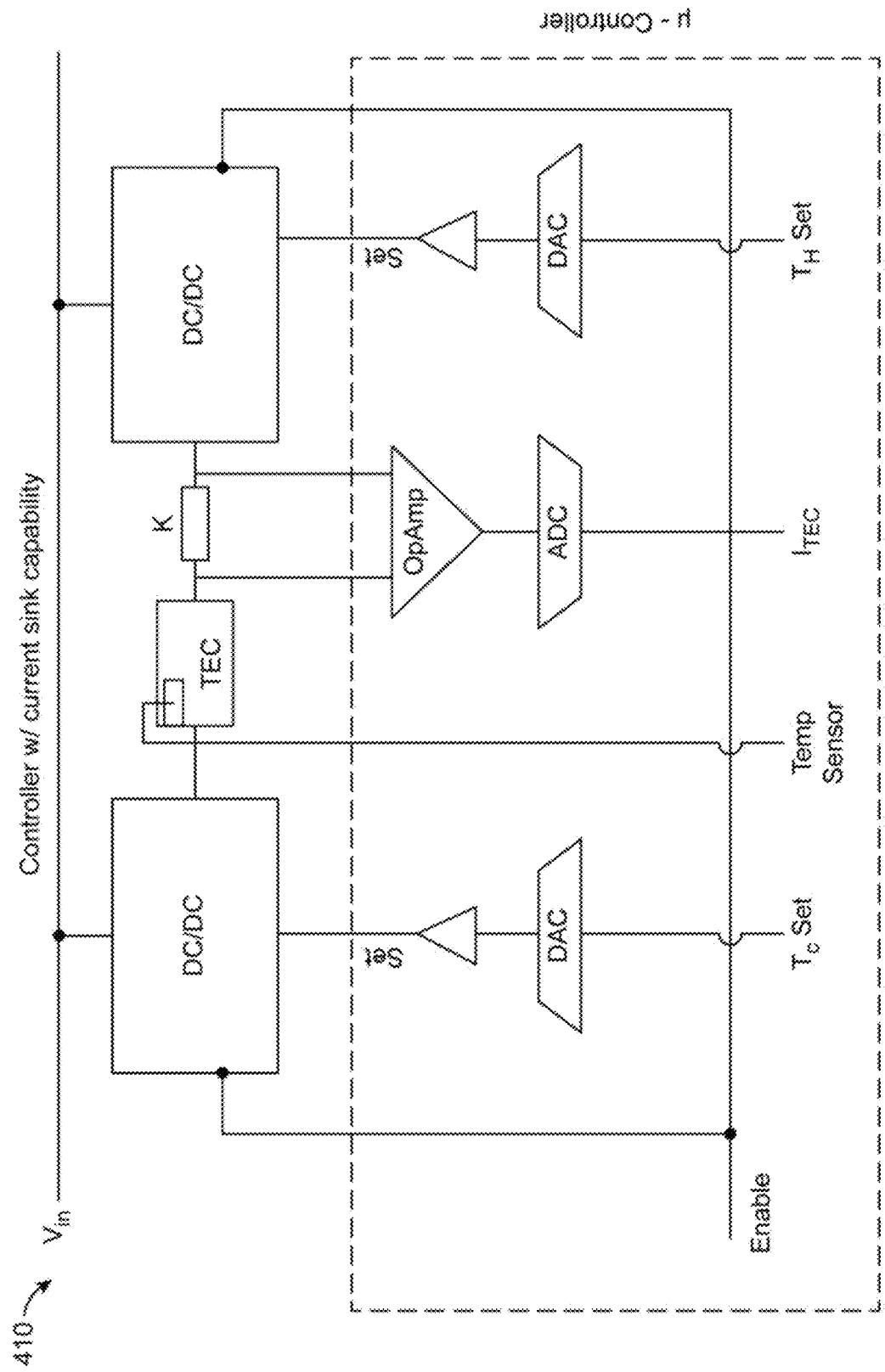
FIG. 4B is a schematic of a thermoelectric control architecture with a current sink capacity, according to an embodiment.
Figure 12A:
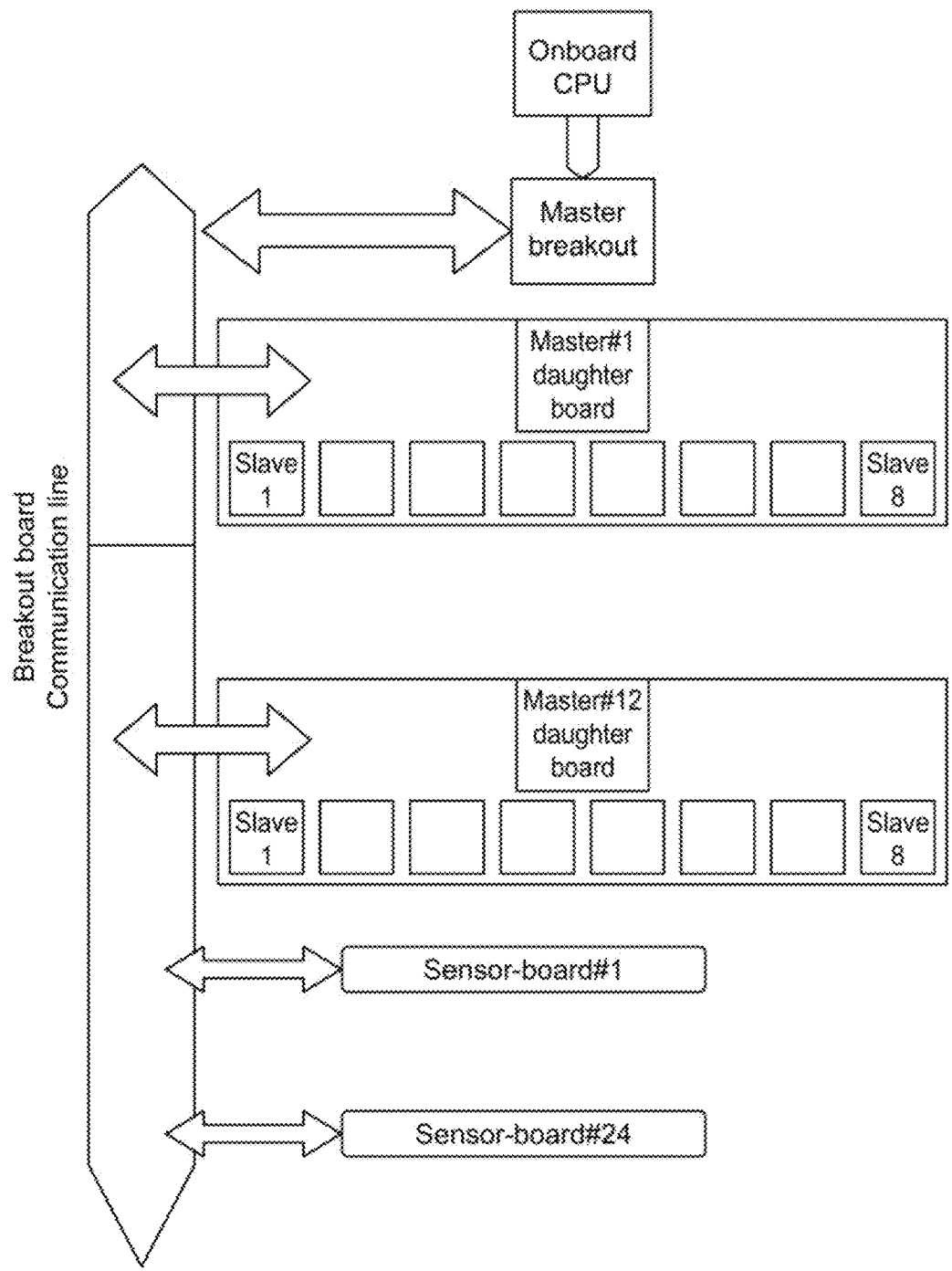
FIGS. 12A-12B show example schematics of control architectures, according to some embodiments.
Figure 12B:
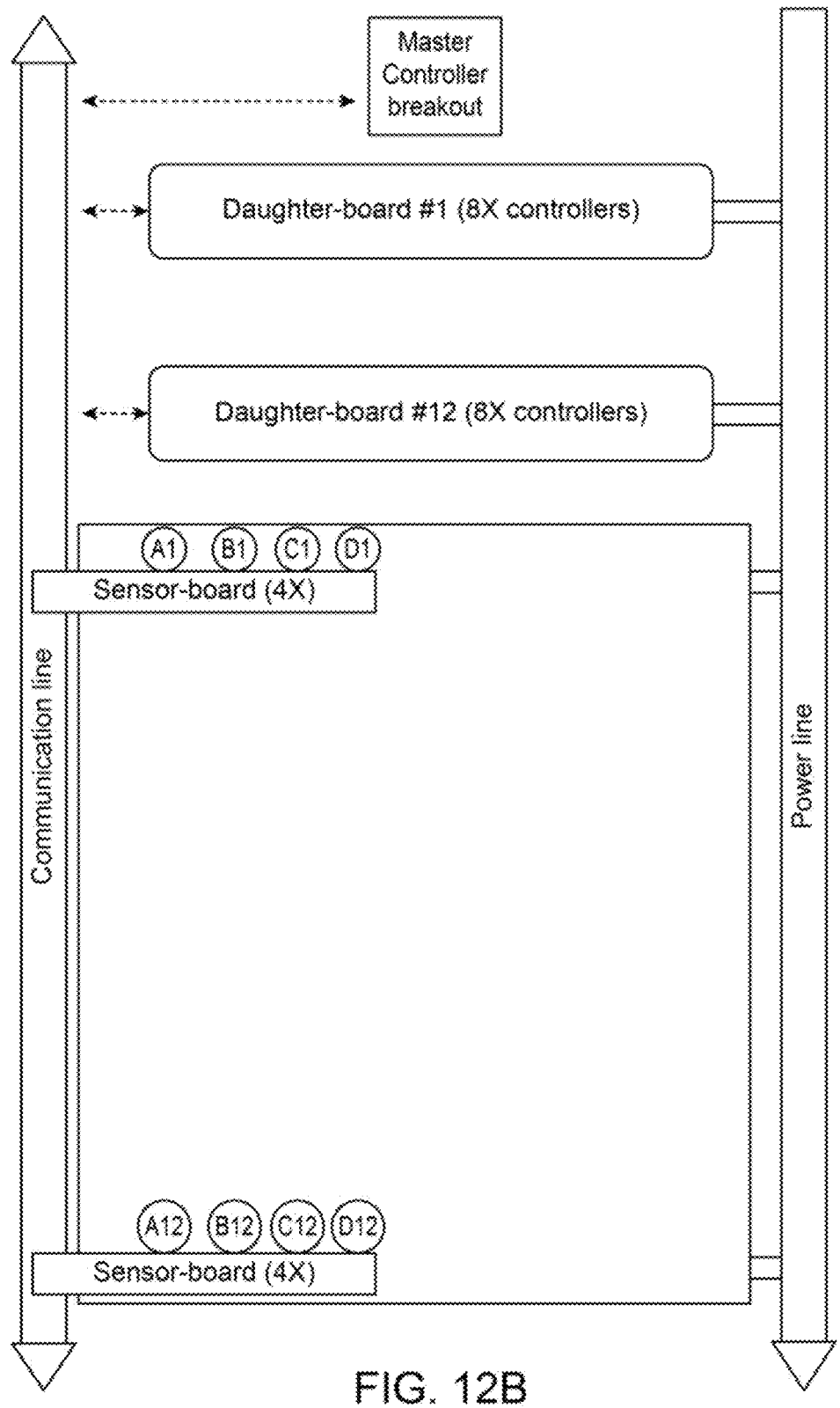

FIG. 4A is a schematic of a thermoelectric control architecture 400, according to an embodiment, while FIG. 4B is a schematic of a thermoelectric control architecture 410 with a current sink capacity, according to an embodiment. The thermoelectric control architecture can be configured to control thermoelectric elements as described elsewhere herein. The thermoelectric control architecture can be based on a DC/DC controller (e.g., a buck controller). The architecture may be configured to fit within a footprint of a device described elsewhere herein. For example, the architecture can be miniaturized to fit within a microwell based device. The thermoelectric control architecture may be addressable by a microcontroller. The microcontroller may be a computer system as described elsewhere herein. The thermoelectric control architecture may be configured to switch one or more thermoelectric elements between heating and cooling modes using a digital switching of two opposed transistors. The switching may occur over a period of at least about 0.1, 0.5, 1, 2, 3, 4, 5, 6, 7, 8, 9, 10, 15, 20, 25, 30, 35, 40, 45, 50, 75, 100, or more milliseconds. The switching may occur over a period of at most about 100, 75, 50, 45, 40, 35, 30, 25, 20, 15, 10, 9, 8, 7, 6, 5, 4, 3, 2, 1, 0.5, 0.1 or less milliseconds. The switching may enable electrical flow within at least about 0.1, 0.5, 1, 2, 3, 4, 5, 6, 7, 8, 9, 10, 15, 20, 25, 30, 35, 40, 45, 50, 75, or more percent of a predetermined target. The switching may enable electrical flow within at most about 75, 50, 45, 40, 35, 30, 25, 20, 15, 10, 9, 8, 7, 6, 5, 4, 3, 2, 1, 0.5, 0.1 or less percent of a predetermined target. The thermoelectric control architecture may be configured to control each element (e.g., control conditions within each well) using a feedback loop. The thermoelectric control architecture may not comprise use of pulse width modulation (PWM). Not using PWM may reduce interference effects and improve the functioning of the control architecture. FIGS. 12A-12B show example schematics of control architectures, according to some embodiments. The control architectures may provide communication between the daughterboards, master control circuitry, and sensors. Each daughterboard may comprise a master microcontroller and at least about 1, 2, 3, 4, 5, 6, 7, 8, 9, 10, or more sub-controllers. Each sub-controller may be connected to a set of sensor boards configured to measure and/or control the temperature of at least about 1, 2, 3, 4, 5, 6, 7, 8, 9, 10, or more reaction chambers. Each sensor board can comprise at least about 1, 2, 3, 4, 5, 6, 7, 8, 9, 10, 11, 12, 13, 14, 15, or more temperature sensors (e.g., digital temperature sensors). The temperature sensors can be calibrated (e.g., calibrated by a National Institute of Science and Technology (NIST) tracible sensor). The temperature sensor may be configured to read a temperature with an accuracy of at least about +/− 0.01, 0.05, 0.1, 0.2, 0.3, 0.4, 0.5, 0.6, 0.7, 0.8, 0.9, 1, or more degrees Celsius. The temperature sensor may be configured to read a temperature with an accuracy of at most about +/− 1, 0.9, 0.8, 0.7, 0.6, 0.5, 0.4, 0.3, 0.2, 0.1, 0.05, 0.01, or less degrees Celsius. The measurements of the temperature sensor may be digital measurements. The digital measurements may be configured to avoid the effects of electrical noise (e.g., electromagnetic interference), which can improve the functioning of the temperature sensors and can enable the individual control of the reaction chambers.

The use of the daughterboard architecture may be modular. For example, the daughterboards may be interchangeable. The modular architecture can provide for efficient replacement of damaged parts (e.g., a damaged daughterboard can be replaced by another daughterboard). The modular architecture may allow for swapping daughterboards in a way that does not affect the communications protocol with or functioning of the temperature sensors or elements. The overall communication can be controlled by the master controller (e.g., master microcontroller). Examples of communication protocol buses include, but are not limited to, Serial Peripheral Interface (SPI), Inter-Integrated Circuit (I2C), Universal Asynchronous Receiver/Transmitter (UART), or the like. The communication protocol bus may be in contact with the daughterboard's master controller. Commands and/or data can flow through the bus to the breakout board master controller and then to the main onboard processing unit. The communication and data collection architecture can provide modularity and can be used to address a plurality (e.g., 96) of reaction chambers.

FIG. 5 is a schematic of an addressable control array 500, according to an embodiment. The addressable control may be configured to control a plurality of elements situated as an array. The control array may comprise connecting one or more elements to a single microcontroller. The elements may be connected via a serial bus (e.g., serial peripheral interface (SPI), I2C, etc.). The array may comprise a plurality of microcontrollers each connected to an additional controller. For example, a series of micro controllers can be connected to another microcontroller. The additional controller and/or the plurality of microcontrollers can be connected to a master controller. For example, a first microcontroller can control a first plurality of elements and a second microcontroller can control a second plurality of elements. In this example, the two microcontrollers can in turn be connected to the master controller. In another example, a first and second microcontroller can be connected to a third microcontroller while a fourth and fifth microcontroller are connected to a sixth microcontroller. In this example, the third and sixth microcontrollers can be connected to the master controller. The master controller may comprise a computer system as described elsewhere herein. For example, the master controller can comprise a microcontroller. In another example, the master controller can comprise a field programmable gate array (FPGA). At least about 1, 2, 3, 4, 5, 6, 7, 8, 9, 10, 15, 20, 25, 30, 35, 40, 45, 50, or more elements can be connected to a single microcontroller. At most about 50, 45, 40, 35, 30, 25, 20, 15, 10, 9, 8, 7, 6, 5, 4, 3, 2, or 1 element can be connected to a single microcontroller. At least about 1, 2, 3, 4, 5, 6, 7, 8, 9, 10, 15, 20, 25, 30, 35, 40, 45, 50, or more microcontrollers can be connected to another microcontroller. At most about 50, 45, 40, 35, 30, 25, 20, 15, 10, 9, 8, 7, 6, 5, 4, 3, 2, or 1 microcontroller can be connected to another microcontroller. At least about 1, 2, 3, 4, 5, 6, 7, 8, 9, 10, 15, 20, 25, 30, 35, 40, 45, 50, or more microcontrollers can be connected to the master controller. At most about 50, 45, 40, 35, 30, 25, 20, 15, 10, 9, 8, 7, 6, 5, 4, 3, 2, or 1 microcontroller can be connected to the master controller.

Figure 9:
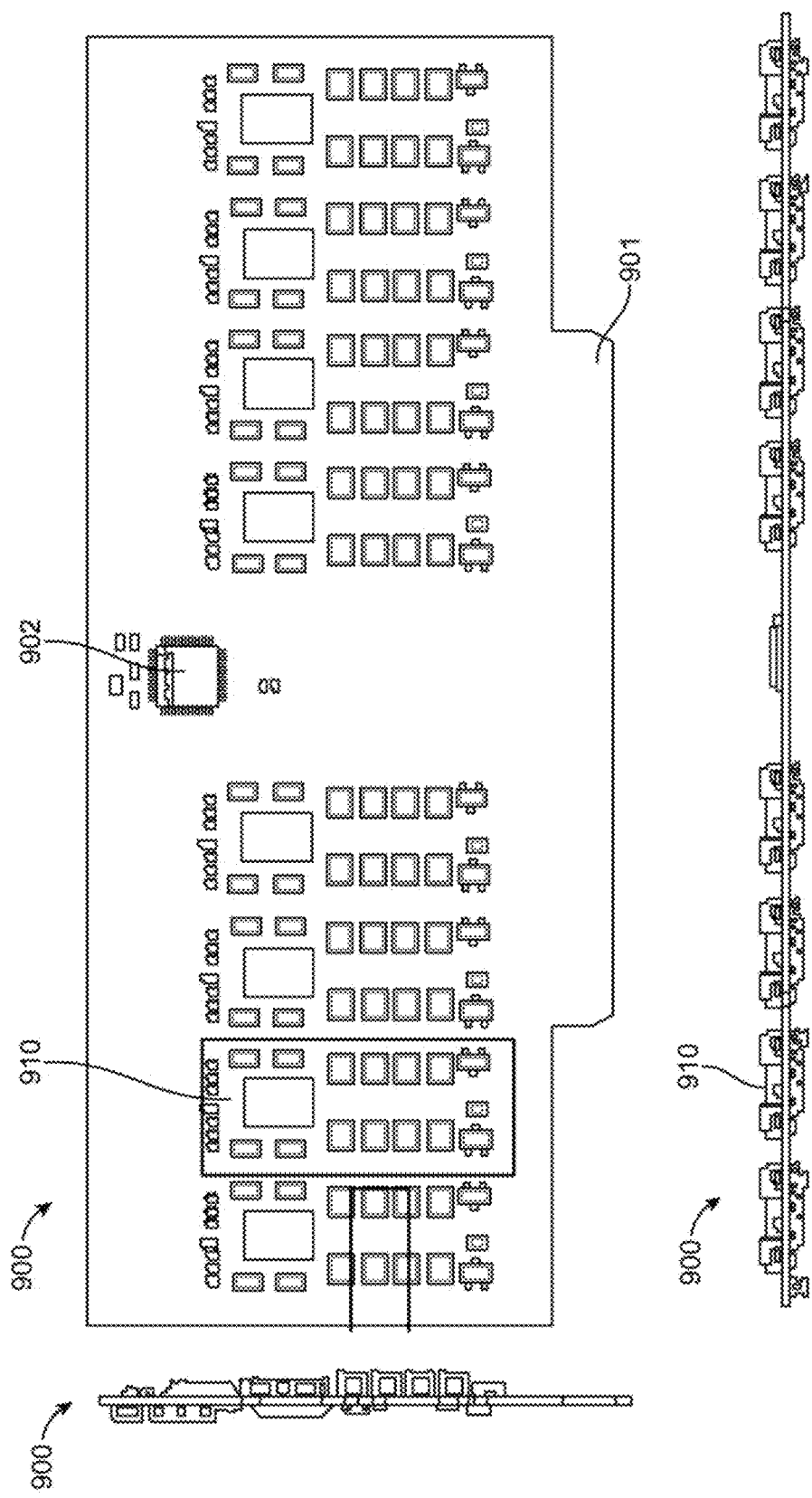
FIG. 9 is an example of a plurality of views of a controller daughterboard, according to some embodiments.

FIG. 9 is an example of a plurality of views of a controller daughterboard 900, according to some embodiments. The controller daughterboard may be configured to perform the methods described elsewhere herein. For example, the daughterboard can be configured to control at least a temperature in a single well of a multi-well plate. The controller daughterboard can comprise controller circuitry 910. The controller circuitry may be configured to control a temperature of a single well. For example, the daughterboard 900 can comprise 8 sets of controller circuitry as shown. A controller daughterboard may comprise at least about 1, 2, 3, 4, 5, 6, 7, 8, 9, 10, 15, 20, 30, 40, 50, 60, 70, 80, 90, 96, or more sets of control circuitry 910. A controller daughterboard may comprise at most about 96, 90, 80, 70, 60, 50, 40, 30, 20, 10, 9, 8, 7, 6, 5, 4, 3, 2, or fewer sets of control circuitry. The controller daughterboard may comprise an interface 901. The interface may be configured to permit addressing of the various components of the daughterboard from a device the daughterboard is interfaced with. For example, a plurality of contacts can be positions on the interface to permit communication between a system and a daughterboard. The daughterboard may comprise one or more microprocessors 902. The one or more microprocessors may be configured as intermediaries between the control circuitry and the system. For example, a microprocessor can be configured to interpret signals from the system to provide output electrical signals to the control circuitry.

In some cases, the control circuitry may comprise one or more switch buck regulators. The switch buck regulators may have an efficiency of at least about 50, 60, 70, 80, 90, 95, 96, 97, 98, 99, or more percent. The switch buck regulators may have an efficiency sufficient to enable the presence of individual thermal elements as described elsewhere herein while maintaining a power budget that can be supplied by, for example, a wall plug. The devices described elsewhere herein may be configured to provide individual thermal control via thermoelectric elements to at least about 1, 2, 3, 4, 5, 10, 25, 50, 75, 96, 100, 150, 200, 250, 300, 350, 384, 400, 450, 500, or more wells using a single wall plug. The control circuitry may comprise two or more switching buck converters controlled externally by one or more microcontrollers. Such a design may not use an H-bridge. Not using an H-bridge may provide improved efficiency (e.g., improved due to the lower loss profile of not having the transistors of the H-bridge). Use of an external microcontroller may enable reduced losses by turning off the buck converters prior to turning off the transistors. In some cases, the daughterboard can comprise 8 sets of controller circuitry in an area of at most about 10,000, 9,500, 9,000, 8,500, 8,154, 8,000, 7,500, 7,000, 6,500, 6,000, 5,500, 5,000, 4,500, 4,000, 3,000, 2,000, 1,000 or fewer centimeters squared.

Figure 10:
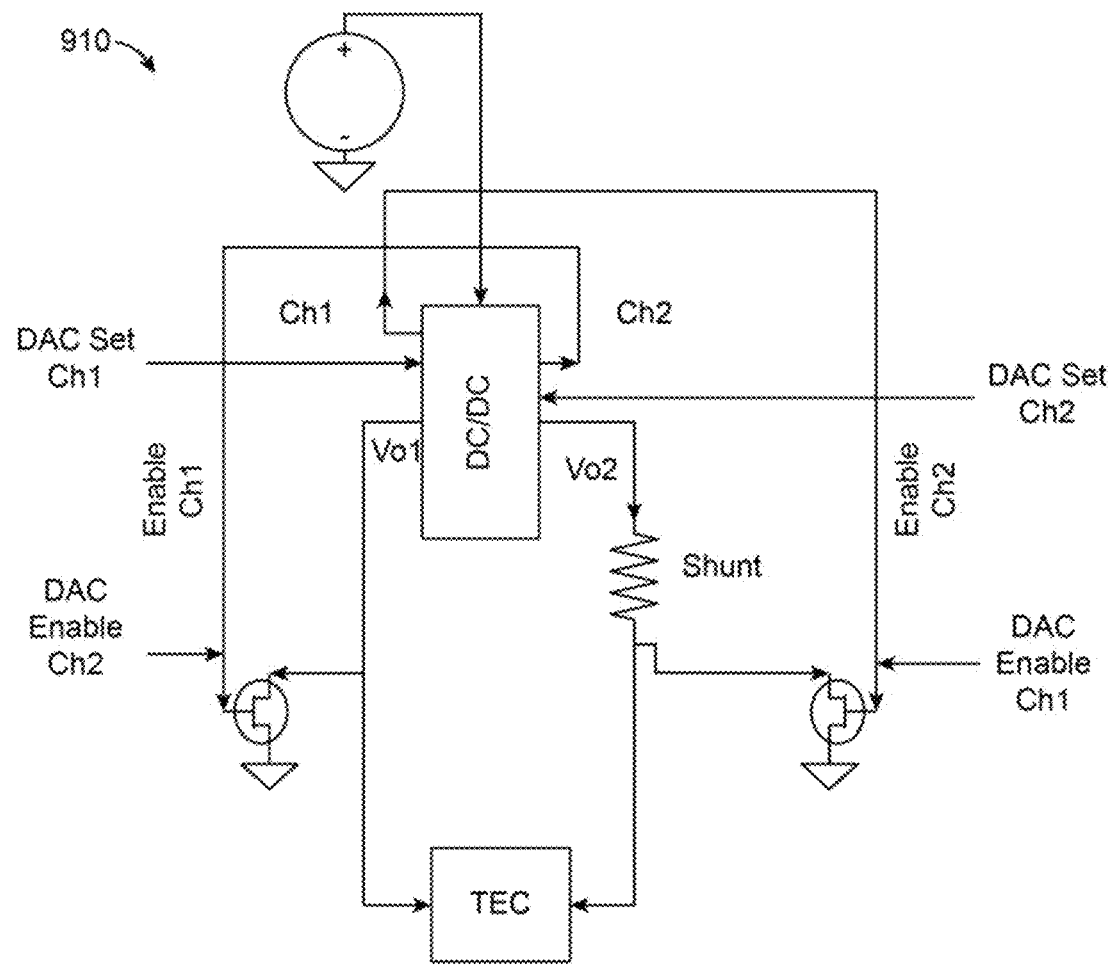
FIG. 10 is an example of a control circuitry, according to some embodiments.

FIG. 10 is an example of a control circuitry 910, according to some embodiments. The TEC may be a thermal element as described elsewhere herein (e.g., a thermoelectric element). The control circuitry may be configured to control a temperature of a single thermal element. For example, each thermal element of a system may have a corresponding set of control circuitry. The control circuitry may be configured to take an input signal from, for example, one or more microprocessors and convert the input signal into a temperature change in the thermal element. The control circuitry may be temperature control circuitry. The control circuitry may be control circuitry for another property (e.g., gas conditions, stirring, etc.).

Figure 11:
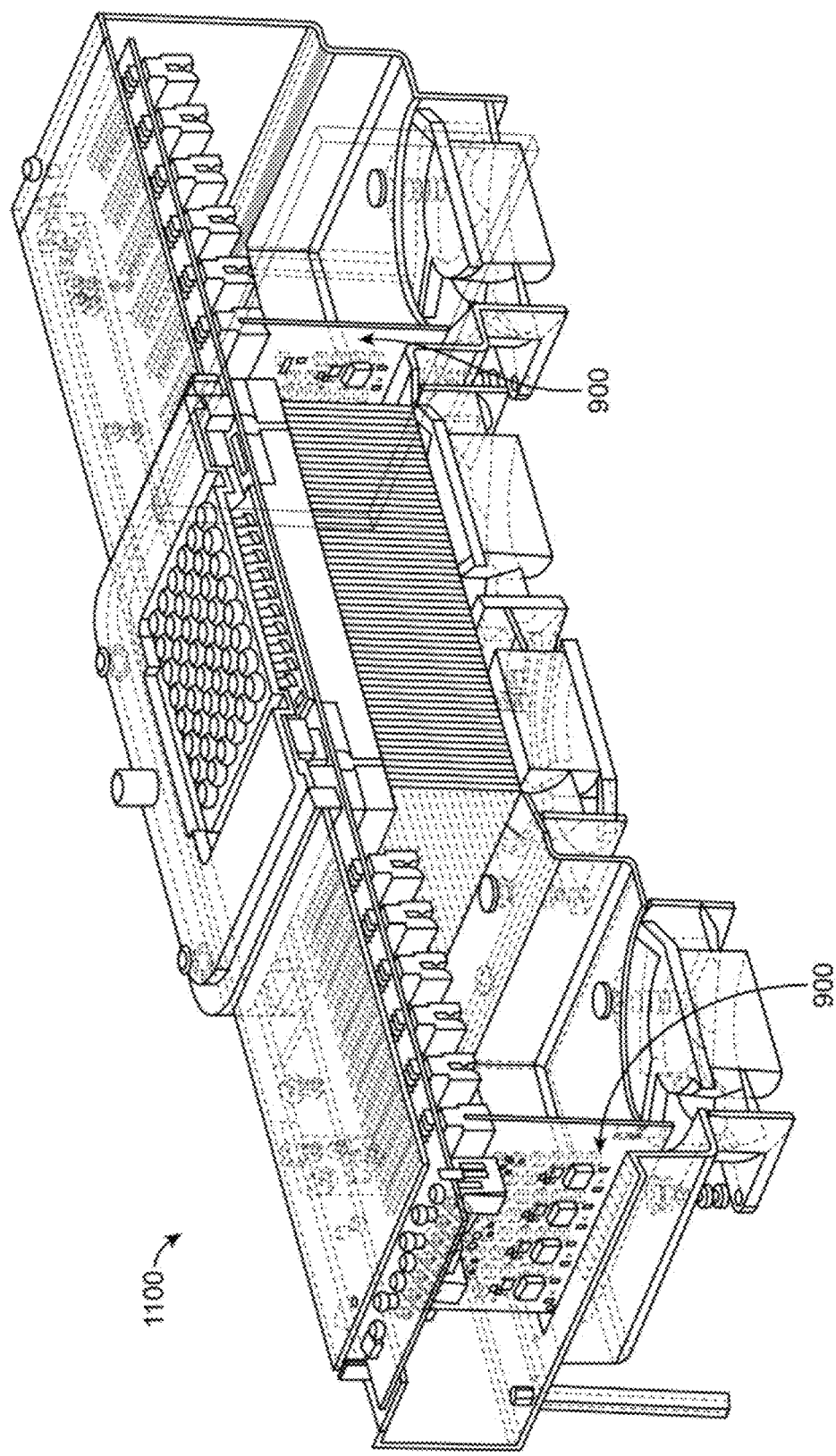
FIG. 11 is a cut away example of a system as described elsewhere herein, according to some embodiments

FIG. 11 is a cut away example of a system 1100 as described elsewhere herein, according to some embodiments. For example, the system can be configured to perform the methods described elsewhere herein. The system may comprise a well plate 1101. The well plate may be as described elsewhere herein. For example, the well plate may be a 96 well plate. Each well of the well plate 1101 may be configured to have an individually controlled temperature as described elsewhere herein. The individual control of the temperature may be achieved at least in part through use of one or more controller daughterboards 900. The controller daughterboards may be interfaced into the system via ports 1103. The ports may be configured to couple to the controller daughterboards to provide electrical contact between the thermal elements of the systems and the control circuitry of the daughterboards. The use of ports may enable switching the controller daughterboards (e.g., for maintenance, for different functionalities, etc.). The use of ports may enable changes to the system configuration over time (e.g., addition or subtraction of control channels, etc.). The system may be configured with a number of daughterboards such that each well of the well plate is coupled to control circuitry. For example, the system can be configured with daughterboards comprising control circuitry such that there is a control circuit for every thermal element of the system.

The system may comprise a heatsink 1102. The heatsink may be configured as described elsewhere herein. For example, the heatsink can be configured to aid in the thermal equilibrium (e.g., heating and/or cooling) of a thermoelectric element. The system may comprise one or more fans 1104. The one or more fans may be configured to provide cooling for the daughterboards, the heatsink, or a combination thereof. For example, the fans can be configured to both cool the control circuitry of the daughterboards as well as the heatsink.

COMPUTER SYSTEMS

Figure 6:
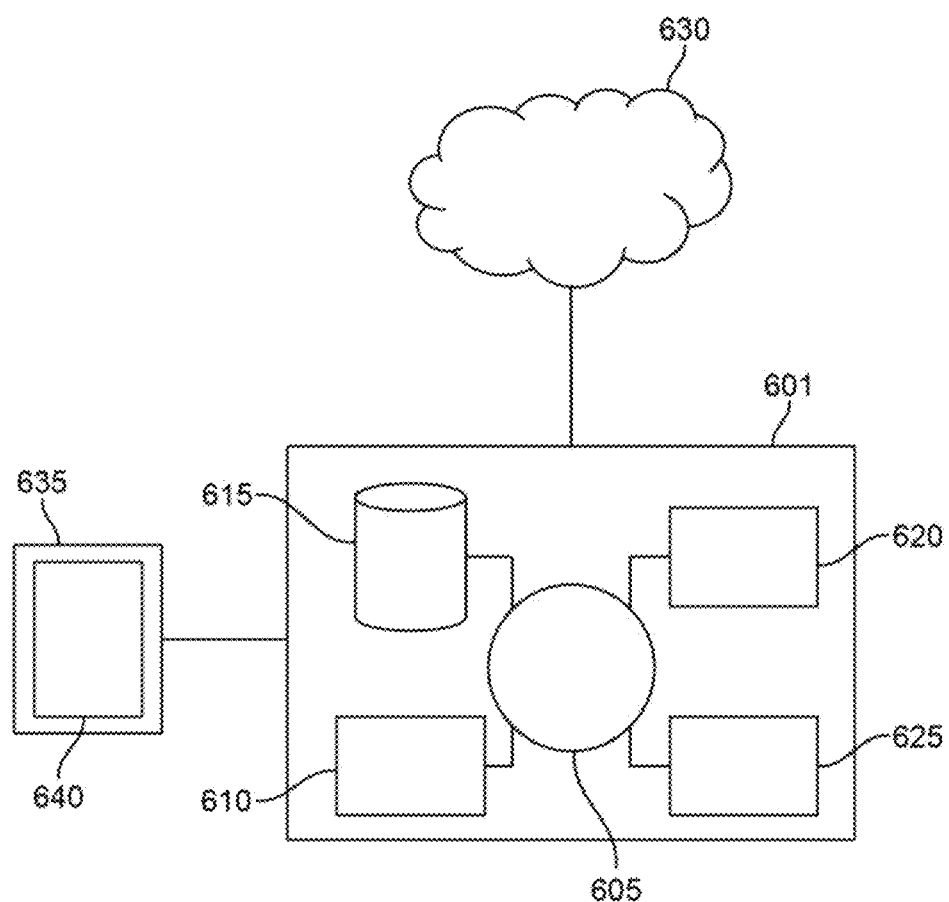
FIG. 6 shows a computer system that is programmed or otherwise configured to implement methods provided herein.

The present disclosure provides computer systems that are programmed to implement methods of the disclosure. FIG. 6 shows a computer system 601 that is programmed or otherwise configured to implement the methods and/or interface with the devices of the present disclosure. The computer system 601 can regulate various aspects of the present disclosure, such as, for example, regulate conditions within a chamber, monitor signals from the chamber, etc. The computer system 601 can be an electronic device of a user or a computer system that is remotely located with respect to the electronic device. The electronic device can be a mobile electronic device.

The computer system 601 includes a central processing unit (CPU, also "processor" and "computer processor" herein) 605, which can be a single core or multi core processor, or a plurality of processors for parallel processing. The computer system 601 also includes memory or memory location 610 (e.g., random-access memory, read-only memory, flash memory), electronic storage unit 615 (e.g., hard disk), communication interface 620 (e.g., network adapter) for communicating with one or more other systems, and peripheral devices 625, such as cache, other memory, data storage and/or electronic display adapters. The memory 610, storage unit 615, interface 620 and peripheral devices 625 are in communication with the CPU 605 through a communication bus (solid lines), such as a motherboard. The storage unit 615 can be a data storage unit (or data repository) for storing data. The computer system 601 can be operatively coupled to a computer network ("network") 630 with the aid of the communication interface 620. The network 630 can be the Internet, an internet and/or extranet, or an intranet and/or extranet that is in communication with the Internet. The network 630 in some cases is a telecommunication and/or data network. The network 630 can include one or more computer servers, which can enable distributed computing, such as cloud computing. The network 630, in some cases with the aid of the computer system 601, can implement a peer-to-peer network, which may enable devices coupled to the computer system 601 to behave as a client or a server.

The CPU 605 can execute a sequence of machine-readable instructions, which can be embodied in a program or software. The instructions may be stored in a memory location, such as the memory 610. The instructions can be directed to the CPU 605, which can subsequently program or otherwise configure the CPU 605 to implement methods of the present disclosure. Examples of operations performed by the CPU 605 can include fetch, decode, execute, and writeback.

The CPU 605 can be part of a circuit, such as an integrated circuit. One or more other components of the system 601 can be included in the circuit. In some cases, the circuit is an application specific integrated circuit (ASIC).

The storage unit 615 can store files, such as drivers, libraries and saved programs. The storage unit 615 can store user data, e.g., user preferences and user programs. The computer system 601 in some cases can include one or more additional data storage units that are external to the computer system 601, such as located on a remote server that is in communication with the computer system 601 through an intranet or the Internet.

The computer system 601 can communicate with one or more remote computer systems through the network 630. For instance, the computer system 601 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 601 via the network 630.

Methods as described herein can be implemented by way of machine (e.g., computer processor) executable code stored on an electronic storage location of the computer system 601, such as, for example, on the memory 610 or electronic storage unit 615. The machine executable or machine readable code can be provided in the form of software. During use, the code can be executed by the processor 605. In some cases, the code can be retrieved from the storage unit 615 and stored on the memory 610 for ready access by the processor 605. In some situations, the electronic storage unit 615 can be precluded, and machine-executable instructions are stored on memory 610.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 601, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 601 can include or be in communication with an electronic display 635 that comprises a user interface (UI) 640 for providing, for example, results of a PCR reaction from a chamber. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 605. The algorithm can, for example, determine that a PCR reaction has completed and halt the reaction within a single chamber.

The following examples are illustrative of certain systems and methods described herein and are not intended to be limiting.

Example 1—Normalization of a Sample Using a Fluorescence Endpoint

Figure 7:
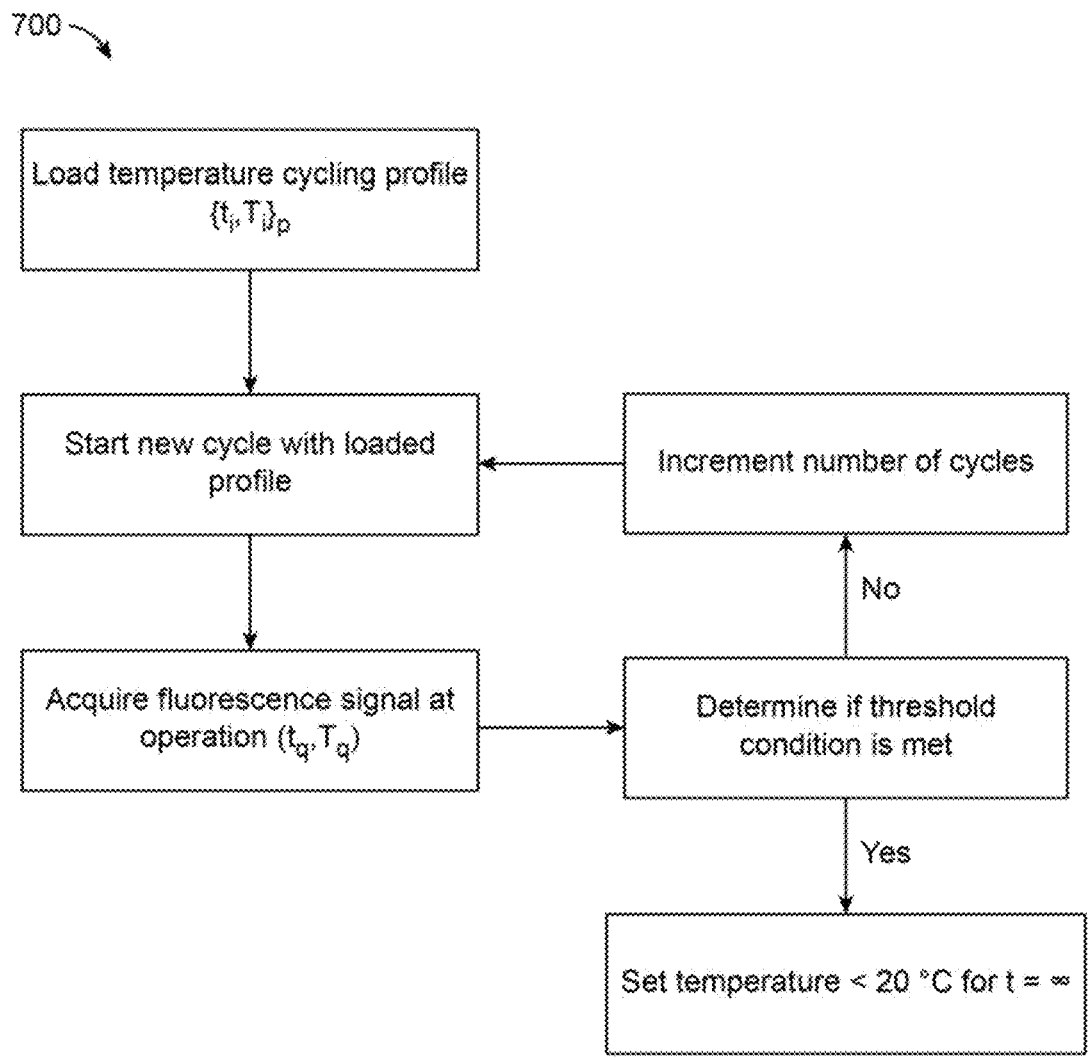
FIG. 7 is a flow chart of control logic for a chamber, according to an embodiment.

FIG. 7 is a flow chart of control logic 700 for a chamber, according to an embodiment. The logic may begin with loading a temperature cycling profile $\{t_i, T_i\}_p$. The temperature cycling profile may comprise p pairs of time and temperature points $\{t_i, T_i\}$. The temperature cycling profile may be configured to enable a performance of a PCR reaction as described elsewhere herein. For example, the temperature cycling profile, when performed, can result in a cycle of PCR being performed. Next, a new cycle can be performed with the loaded profile. Upon or before completion of the cycle, the fluorescence signal can be acquired. For example, the signal can be acquired at a quantification operation $\{t_q, T_q\}$. The fluorescence signal can be acquired as described elsewhere herein. Upon receipt of the fluorescence signal, one or more computer processors as described elsewhere herein can determine if a threshold condition (e.g., a predetermined normalization threshold, a predetermined level of fluorescent intensity, etc.). If the fluorescence signal has not reacted the threshold condition, the number of cycles can be incremented and the process repeated. If the fluorescence signal meets the threshold condition, the logic can stop the PCR reaction in the chamber by setting the temperature to <20° C. Since, as described elsewhere herein, different chambers can be controlled independently, the completion of one reaction does not mean that other reactions will not continue as described above. For example, a first chamber can meet the threshold condition while a second chamber does not. In this example, the reaction in the first chamber can be halted by reducing the temperature while the reaction in the second chamber can be unaffected.

Figure 8:
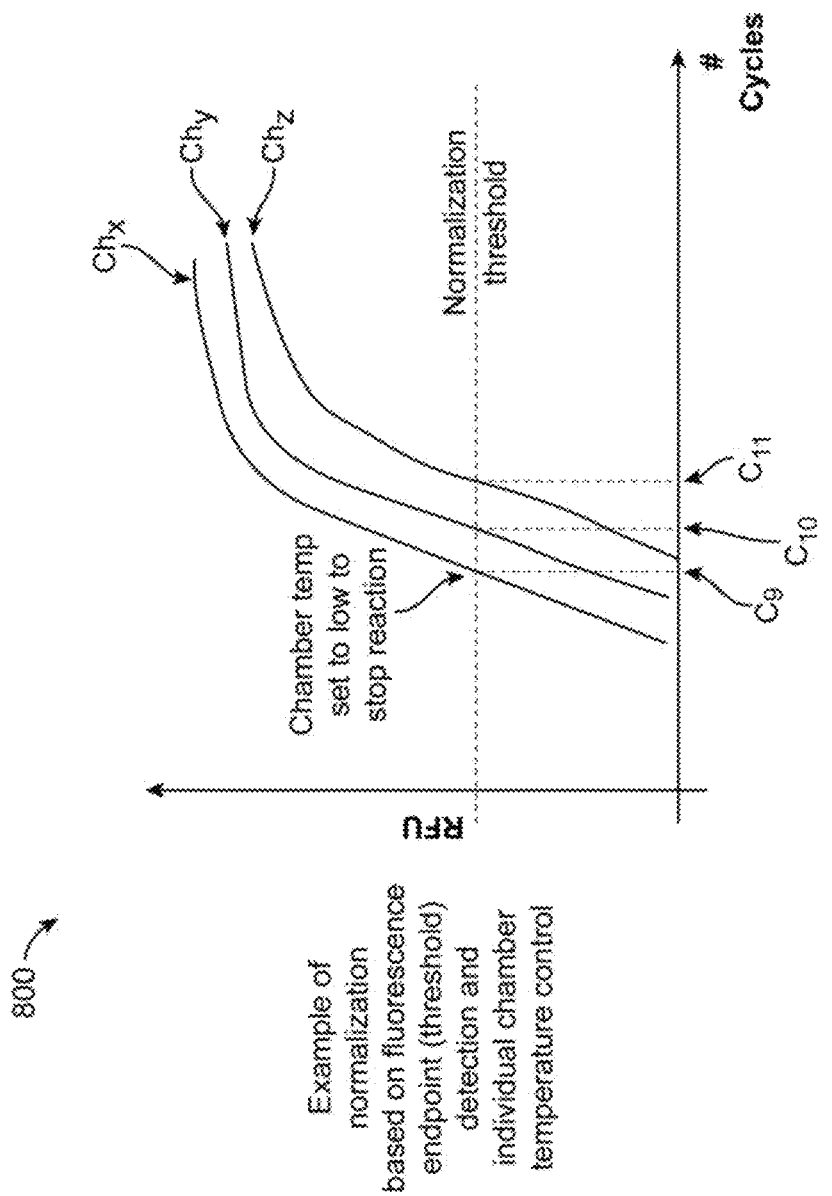
FIG. 8 is an example of a normalization based on a fluorescence endpoint, according to an embodiment.

FIG. 8 is an example of a normalization based on a fluorescence endpoint, according to an embodiment. The plot 800 may be a plot of relative fluorescent intensity on the y-axis against the number of PCR cycles performed on the x-axis. The number of cycles to reach an endpoint may be different for different chambers (e.g., chambers $Ch_x$, $Ch_y$, and $Ch_z$). In this example, $Ch_x$ can reach a predetermined fluorescence signal threshold after 9 cycles, while $Ch_y$ takes 10 and $Ch_z$ takes 11. For each chamber, once the chamber reaches the predetermined normalization threshold, the chamber can be deactivated using the individual temperature control for each chamber. For example, each chamber can be cooled to halt a PCR reaction after the signal from the chamber exceeds the normalization threshold.

Example 2—Thermal Performance of Adjacent Wells

Figure 13:
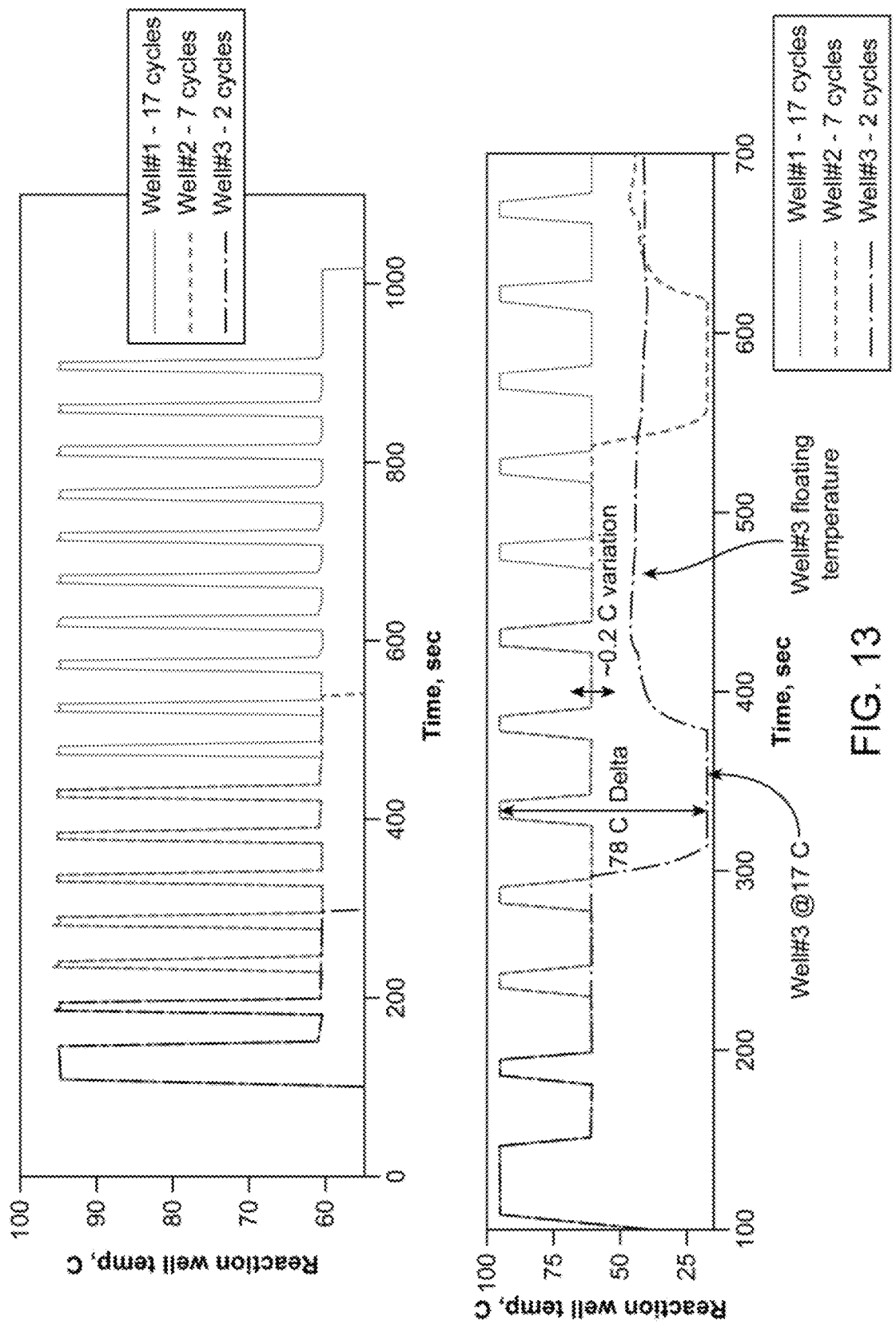
FIG. 13 is an example of the thermal performance of a plurality of adjacent individually controlled wells, according to some embodiments.

FIG. 13 is an example of the thermal performance of a plurality of adjacent individually controlled wells, according to some embodiments. In initial time points (e.g., at early times on the graph), the three wells can be performing the same temperature cycling protocol (e.g., cycling between 95 and 60 degrees Celsius). The different wells may show similar performance when under the same protocol, as evidenced by the similar temperature curves. After 2 cycles, the third well may no longer be under the same temperature protocol. For example, the third well can be set to dwell at 60 degrees Celsius while the other two wells continue cycling. The data of FIG. 13 may show that the wells of the plate are individually addressable, with each well being able to be put at a predetermined temperature independent of the other wells. This may be further evidenced by the performance of wells 2 and 1, which are cycled for 7 and 17 cycles, respectively.

The lower plot of FIG. 13 may show an expanded temperature and time range for the three wells. After being held at 60 degrees Celsius, well 3 can be cooled to 17 degrees (e.g., below ambient temperature) while the other two wells continue the elevated temperature cycling. Despite being adjacent (e.g., <10 millimeters distant) to the elevated temperature wells, well 3 can be maintained at a lower temperature due to the thermal isolation of the well. Such a capacity can provide the ability to individually control the reaction conditions of a given well, which can permit customization of the reaction to the given well. After a time, the temperature control of well 3 can be turned off, which can result in the observed temperature drift of well 3. Wells 1 and 2 can be kept at similar temperatures (e.g., about 0.2 degrees Celsius difference) until well 2 is cooled and subsequently allowed to drift.

Figure 14:
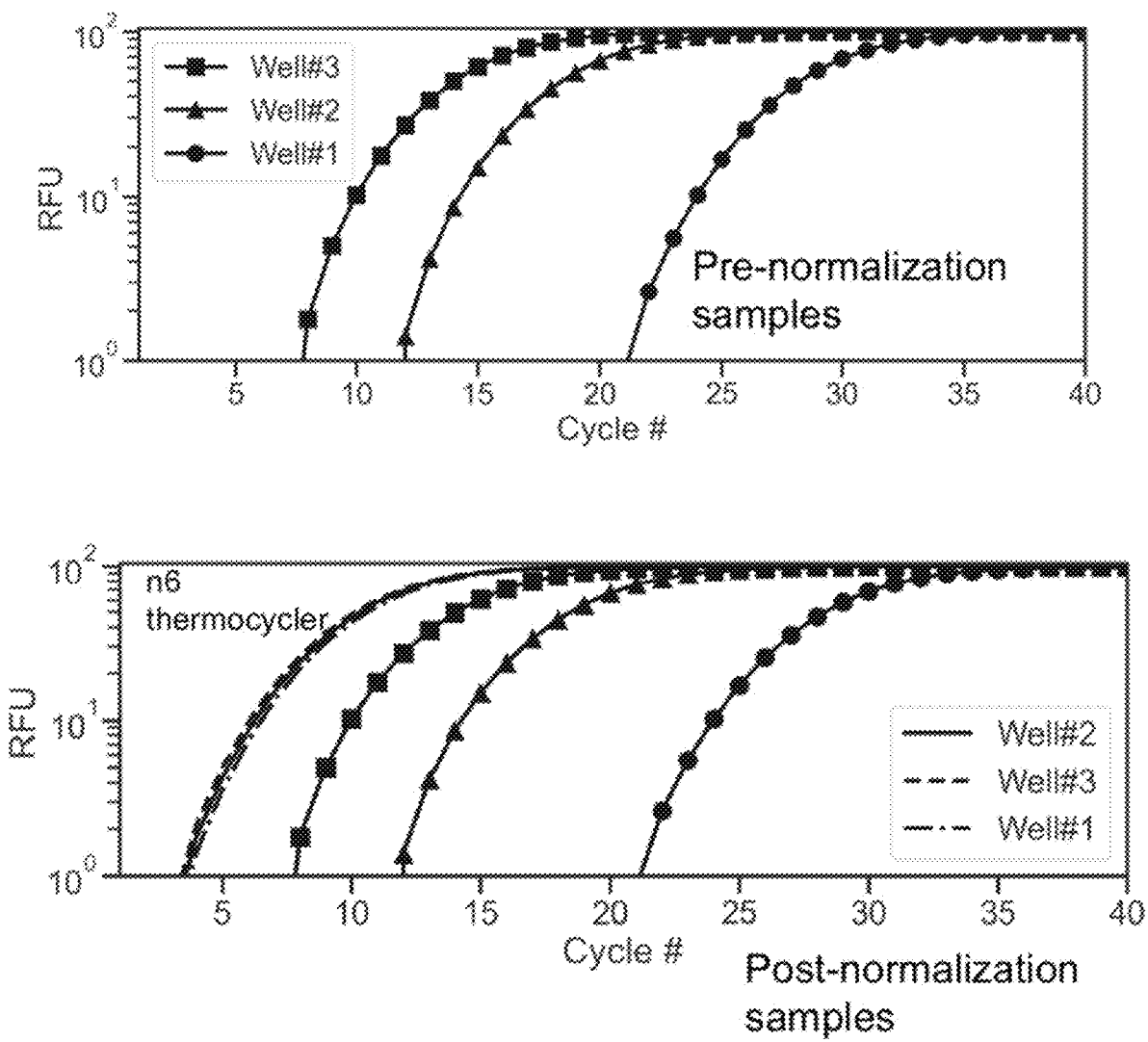
FIG. 14 shows the performance comparison of individually controlled wells versus non-individually controlled wells, according to some embodiments.

FIG. 14 shows the performance comparison of individually controlled wells versus non-individually controlled wells, according to some embodiments. In some cases, un-normalized PCR reactions can generate different amounts of signal depending on a number of factors, such as, for example, reaction conditions, reagent loading, initial loading of the target nucleic acid, etc. Such inconsistencies can generate curves such as those present in the upper plot of FIG. 14. In these plots, the reactions occurring in the various wells can provide different amounts of signal after different numbers of cycles. In some cases, individual control of the wells can enable normalization of the wells to provide a similar amount of signal from different wells, as shown in the lower plot of FIG. 14. In the lower plot, the wells can be normalized (e.g., by controlling the individual conditions of the wells) to provide a similar amount of signal for a given number of cycles.

Example 3—Optimization of Annealing Temperature

Figure 22:
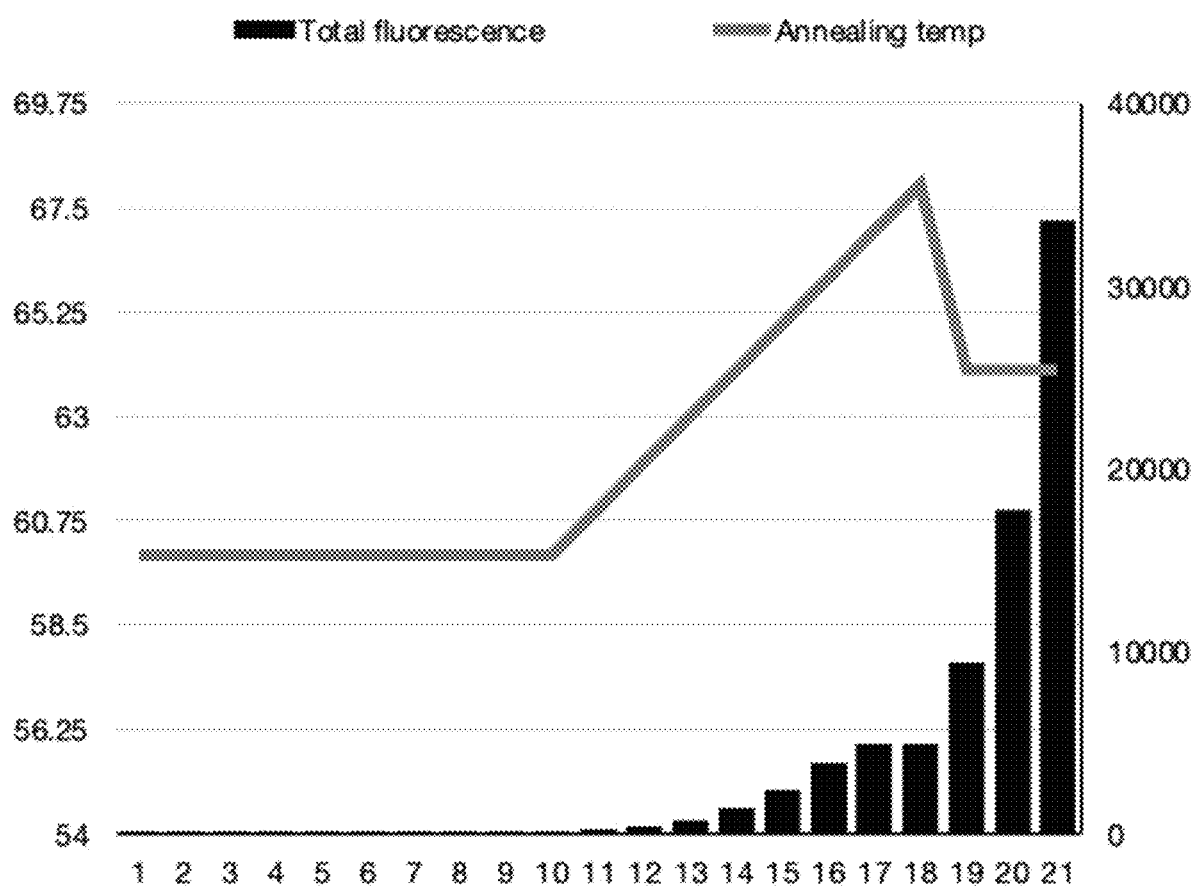
FIG. 22 shows an example of an annealing temperature optimization experiment, according to some embodiments.

FIG. 22 shows an example of an annealing temperature optimization experiment, according to some embodiments. In some cases, performing an amplification at an optimal annealing temperature can improve the signal collected from the amplification reaction, as well as improve the speed at which the reaction is performed. An optimal annealing temperature can be determined on a per-reaction basis, where a test reaction can be performed, and subsequent reactions can utilize the optimal temperature determined by the test reaction. In this way, the optimization of the annealing temperature may be performed once for a plurality of reactions.

The annealing temperature optimization may be enabled by use of real-time monitoring of the well the reaction is being performed in, as well as control of the reaction conditions within the well. A system described elsewhere herein may be configured to perform a plurality of optimization reactions at a same time. For example, each well of a well plate can comprise a different optimization reaction.

In some cases, an optimization reaction can comprise beginning an amplification reaction at a first temperature (e.g., the 60 degrees Celsius of FIG. 22). The amplification reaction can be repeated for a plurality of cycles until a signal is detected from the amplification reaction (e.g., cycle 10 of FIG. 22). Once the signal is detected from the amplification reaction, the temperature of the reaction can be increased with each subsequent cycle. As the temperature is increased, the rate of increase of the signal (e.g., fluorescent signal) may increase. At some point (e.g., cycle 18 of FIG. 22), the signal increase may stop. This may be due to the temperature of the reaction being set too high, and thus the optimal temperature may be determined (e.g., the temperature one cycle lower than the temperature that caused the signal to stop). The optimal temperature may then be applied for subsequent cycles, as well as for the processing of subsequent reactions.

Example 3—Multi-Well Temperature Gradients

Figure 23:
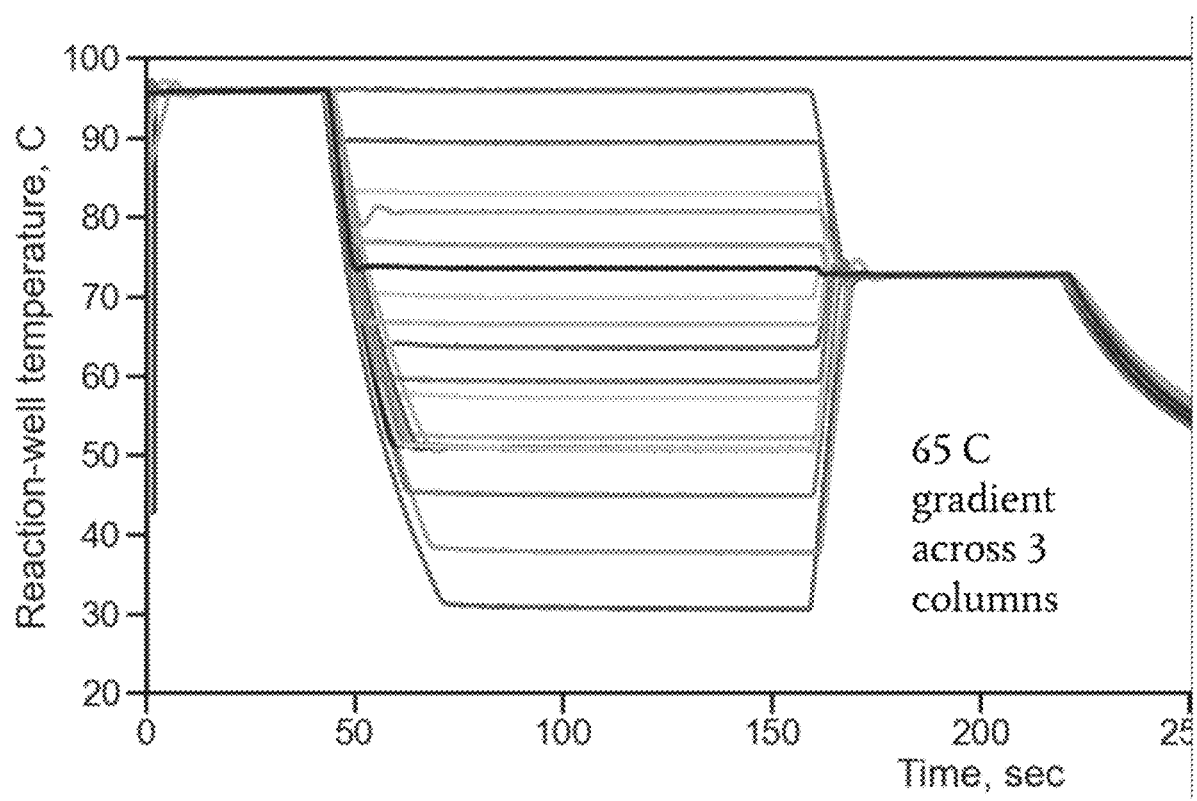
FIG. 23 shows a plot of temperature profiles obtained within 24 wells executing a protocol with a 65 degree Celsius linear gradient, according to some embodiments.

FIG. 23 shows a plot of temperature profiles obtained within 24 wells executing a protocol with a 65 degree Celsius linear gradient, according to some embodiments. In this example, 24 wells were set to temperatures according to FIGS. 24A-24B. For example, FIG. 24B can show a temperature gradient over 24 wells across 3 columns. In each case, the wells were all set to 95 degrees Celsius at first and all set to 72 degrees Celsius to finish. The wells were set to a gradient according to FIG. 24B between the 95 degree Celsius and 72 degree Celsius settings spanning 30 to 80 degrees Celsius. As observed in FIG. 23, no cross-talk between the wells is seen, demonstrating individual control of the thermal properties of each of the wells.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations, or equivalents. It is intended that the following claims define the scope of the invention and that methods and structures within the scope of these claims and their equivalents be covered thereby.

What is claimed is:

1. A method for performing a polymerase chain reaction (PCR) analysis of a first sample containing or suspected of containing an analyte, comprising:
   (a) providing said first sample to a first location of a substrate, wherein said first location has a first volume configured to retain said first sample and permit said first sample to be subjected to a condition for a first PCR reaction, wherein said substrate further comprises a second location comprising a second sample undergoing a second PCR reaction;
   (b) using a first element disposed adjacent to said first location to affect said condition in said first location to thereby initiate said first PCR reaction using said first sample, wherein said first PCR reaction generates a signal or signal change which is indicative of a property associated with said analyte;
   (c) using a second element operably coupled to said first element to adjust an operating condition of said first element at least partially in response to said signal or signal change, to thereby affect said condition in said first location; and
   (d) adjusting said operating condition of said first element to decrease a rate of said first PCR reaction upon said signal or signal change reaching a predetermined threshold, wherein said second PCR reaction continues within said second location after said first PCR reaction in said first location is stopped.

2. The method of claim 1, wherein prior to (d), a cycle number in said first location is different from a cycle number in said second location.

3. The method of claim 1, wherein said substrate is a multi-well plate.

4. The method of claim 1, wherein said first location and said second location are spatially distinguishable and independently addressable.

5. The method of claim 1, wherein said method does not comprise pre-normalization.

6. The method of claim 1, wherein said method does not comprise pre-quantification.

7. The method of claim 1, wherein said predetermined threshold is a predetermined normalization threshold.

8. The method of claim 1, wherein said predetermined threshold is a predetermined level of fluorescent intensity.

9. The method of claim 1, wherein said condition is a temperature condition.

10. The method of claim 1, wherein said condition is a magnetic field condition.

11. The method of claim 1, wherein said condition is an optical condition.

12. The method of claim 1, wherein said signal or signal change comprises an optical signal or optical signal change.

13. The method of claim 3, wherein said first location and said second location are respective wells comprised in said multi-well plate.

14. The method of claim 1, wherein said property is a presence, an absence, an amount, or a concentration of said analyte.

15. The method of claim 14, wherein said presence or said absence of said analyte is determined with a sensitivity of at least about 90%.

16. The method of claim 14, wherein said presence or said absence of said analyte is determined with a specificity of at least about 90%.

17. The method of claim 14, wherein said presence or said absence of said analyte is determined with an accuracy of at least about 90%.

18. The method of claim 1, wherein said first element is a thermoelectric heating element.

19. The method of claim 1, wherein said second element is an optical source.

20. The method of claim 1, wherein said first sample does not comprise an internal standard.

* * * * *